US007306740B2

(12) United States Patent
Freund

(10) Patent No.: US 7,306,740 B2
(45) Date of Patent: Dec. 11, 2007

(54) FAT COLLECTION AND PREPARATION SYSTEM AND METHOD

(75) Inventor: Robert M. Freund, Old Westbury, NY (US)

(73) Assignee: Lipose Corporation, Greenwich, CT (US)

(*) Notice: Subject to any disclaimer, the term of this patent is extended or adjusted under 35 U.S.C. 154(b) by 451 days.

(21) Appl. No.: 10/844,129

(22) Filed: May 11, 2004

(65) Prior Publication Data

US 2005/0123895 A1 Jun. 9, 2005

Related U.S. Application Data

(63) Continuation-in-part of application No. 10/732,125, filed on Dec. 9, 2003, now abandoned.

(51) Int. Cl.
*B01D 17/038* (2006.01)
(52) U.S. Cl. .................. 210/781; 210/806; 494/37; 436/177
(58) Field of Classification Search ............... 604/187, 604/190, 240, 241; 494/16, 36, 37; 436/177; 422/72, 101, 102; 210/781, 806, 515, 516
See application file for complete search history.

(56) References Cited

U.S. PATENT DOCUMENTS

| | | | |
|---|---|---|---|
| 3,596,652 A | | 8/1971 | Winkelman |
| 3,817,389 A | | 6/1974 | Weichselbaum |
| 4,014,797 A | | 3/1977 | Raines et al. |
| 4,119,542 A | | 10/1978 | Yamaoka et al. |
| 4,316,462 A | | 2/1982 | Baker |
| 4,364,832 A | * | 12/1982 | Ballies ................ 210/518 |

(Continued)

FOREIGN PATENT DOCUMENTS

GB 2277464 11/1994

(Continued)

OTHER PUBLICATIONS

Sep. 2000, Byron Medical catalog pages: CAT 137.0 REV 2/00; CAT 138.0 REV 2/00; CAT 143.0 REV 3/00; CAT 144.0 REV 9/00; CAT 141.0 REV 3/00; CAT 142.00 REV Aug. 3, 1998; and CAT 144.1 REV 9/00.

(Continued)

*Primary Examiner*—David A Reifsnyder
(74) *Attorney, Agent, or Firm*—Kaplan Gilman Gibson & Dernier LLP; Matthew B. Dernier

(57) ABSTRACT

System and methods for collecting and preparing fat for autologous fat transplantation. The system includes a centrifuge, syringes, and filtering and transferring assemblies coupled with the syringes. Substances, including oil, fat, and denser substances (tumescent fluid, connective tissue, and other non-fat substances), are harvested into a syringe. A dye is provided or injected in the syringe. Centrifugation of the syringe stratifies the substances into a top oil stratum, a middle fat stratum, and a bottom denser substance stratum. A superficial layer of less viable fat tissue in the middle stratum is highlighted by the dye. Denser substances are filtered out of the syringes during centrifugation. Oil and the less viable fat tissue are removed through a port in the plunger head of the syringe plunger. More viable fat tissue is transferred into smaller syringes through an adapter in the assembly coupled with the syringe and the smaller syringes.

11 Claims, 31 Drawing Sheets

U.S. PATENT DOCUMENTS

| | | | |
|---|---|---|---|
| 4,391,274 A | 7/1983 | Kagan | |
| 4,448,206 A | 5/1984 | Martell | |
| 4,632,672 A | 12/1986 | Kvitrud | |
| 4,660,569 A | 4/1987 | Etherington | |
| 4,702,162 A | 10/1987 | Sontheimer et al. | |
| 4,781,683 A | 11/1988 | Wozniak et al. | |
| 4,820,276 A | 4/1989 | Moreno | |
| 4,958,557 A | 9/1990 | Fiala | |
| 5,002,538 A | 3/1991 | Johnson | |
| 5,125,415 A | 6/1992 | Bell | |
| 5,149,432 A | 9/1992 | Lavin | |
| 5,238,003 A | 8/1993 | Baidwan et al. | |
| 5,255,688 A | 10/1993 | Gilliard | |
| 5,441,487 A | 8/1995 | Vedder | |
| 5,474,675 A | 12/1995 | Kupka | |
| 5,480,484 A | 1/1996 | Kelley et al. | |
| 5,489,266 A | 2/1996 | Grimard | |
| 5,490,453 A | 2/1996 | Mackay | |
| 5,624,402 A | 4/1997 | Imbert | |
| 5,679,154 A | 10/1997 | Kelley et al. | |
| 5,685,864 A | 11/1997 | Shanley et al. | |
| 5,795,477 A | 8/1998 | Herman et al. | |
| 5,807,353 A | 9/1998 | Schmitz | |
| 5,851,201 A | 12/1998 | Ritger et al. | |
| 5,855,230 A | 1/1999 | Guala et al. | |
| 5,865,803 A | 2/1999 | Major | |
| 5,919,169 A | 7/1999 | Grams et al. | |
| 6,190,364 B1 | 2/2001 | Imbert | |
| 6,383,173 B1 | 5/2002 | Hunt | |
| 6,494,896 B1 | 12/2002 | D'Alessio et al. | |
| 6,520,935 B1 | 2/2003 | Jansen et al. | |
| 2001/0035101 A1 | 11/2001 | Ancona et al. | |
| 2002/0143298 A1 | 10/2002 | Marsden | |
| 2002/0182664 A1 | 12/2002 | Dolecek et al. | |
| 2003/0069543 A1 | 4/2003 | Carpenter et al. | |

FOREIGN PATENT DOCUMENTS

| | | |
|---|---|---|
| WO | WO 91/05502 | 5/1991 |

OTHER PUBLICATIONS

Ullmann et al., *Enhancing the Survival of Aspirated Human Fat Injected into Nude Mice*, Plastic and Reconstructive Surgery, vol. 101, No. 7, Jun. 1998, pp. 1940-1944.

Jose Guerrerosantos, *Simultaneous Rhytidoplasty and Lipoinjection: A Comprehensive Aesthetic Surgical Strategy*, Plastic and Reconstructive Surgery, vol. 102, No. 1, Jul. 1998. pp. 191-199.

Har-Shai et al., *An Integrated Approach for Increasing the Survival of Autologous Fat Grafts in the Treatment of Contour Defects*, Plastic and Reconstructive Surgery, vol. 104, No. 4, Sep. 1999, pp. 945-954.

Yuksel et al., *Increased Free Fat-Graft Survival With the Long Term, Local Delivery of Insulin*, Plastic and Reconstructive Surgery, vol. 105, No. 5, Apr. 2000, pp. 1712-1720.

Katz et al., *A Novel Device for the Simple and Efficient Refinement of Liposuctioned Tissue*, Plastic and Reconstructive Surgery, vol. 107, No. 2, Feb. 2001, pp. 595-597.

Boschert et al., *Analysis of Lipocyte Viability After Liposuction*, Plastic and Reconstructive Surgery, vol. 109, No. 2, Feb. 2002, pp. 761-56.

Rubin et al., correspondence to Dr. Hoefflin entitled *Fat Purification: Survival of the Fittest*, Plastic and Reconstructive Surgery, vol. 109, No. 4, Apr. 2002, pp. 1463-1464.

Sydney R. Coleman, *Hand Rejuvenation With Structural Fat Grafting*, Plastic and Reconstructive Surgery, vol. 110, No. 7, Dec. 2002, pp. 1731-1744.

\* cited by examiner

FAT COLLECTION AND PREPARATION SYSTEM AND METHOD

RELATED APPLICATIONS

This application is a continuation-in-part of U.S. application Ser. No. 10/732,125, filed Dec. 9, 2003, now abandoned, which is hereby incorporated by reference in its entirety into this application.

FIELD OF INVENTION

The present invention relates to a fat collection and preparation system and method for harvesting fat from human tissue and preparing harvested fat for injection for cosmetic rejuvenation purposes, including relief of facial aging and wrinkling, as well as for other purposes.

BACKGROUND

In the field of plastic surgery, various substances and techniques are being developed in the area of cosmetic rejuvenation, for, inter alia, relieving facial aging and wrinkling. Current techniques involve the implantation of foreign substances into the affected areas of the recipient. Two foreign substances currently being used in this area are collagen and synthetic materials. Collagen implants involve the injection of the protein substance of the white fibers of (collagenous fibers) of connective tissue, such as skin, tendon, bone and cartilage. Current synthetic implants involve the injection of silicone, cadaver skin, and other synthesized materials. However, collagen and synthetic implants have various downsides, including infection, inflammation, rejection by the recipient, and limited durability of the injected materials. In an effort to eliminate these and other downsides associated with implanting collagen, synthetic or other foreign materials, fat transplantation (or transplantation of fat or fat tissue or cells) is being regarded as the future mainstay of cosmetic rejuvenation.

Fat transplantation involves: (a) harvesting fat tissue, along with other substances surrounding it from a harvesting site; (b) preparing the fat tissue; and then (c) injecting the fat tissue into the affected areas in the recipient. Fat tissue resides in the human body together with blood vessels, and other naturally occurring substances. In order to harvest the fat tissue, a tumescent fluid is first injected into the harvesting site, which may be, e.g., another part of the recipient's body. The tumescent fluid swells or increases the volume of the tissue in the harvesting site, thus reducing blood loss during harvesting, and facilitating the removal of the tissue from the harvesting site. Tumescent fluid currently includes a mixture of salt solution, epinephrine and lidocaine, although other substances may be used in order to accomplish the same effect on the fat tissue. A mixture of fat tissue, tumescent fluid, and oil (created by the body as a result of harvesting trauma), is then harvested from the site under low vacuum pressure into harvesting syringes through specially designed cannulae inserted into the site.

In order to prepare the fat tissue for injection, it must be separated from the other harvested substances in the mixture inside the syringe. Automated centrifuges have been used to segregate the mixture into the three layers of oil, fat tissue (or the fatty layer in the syringe), and tumescent fluid within each harvesting syringe. These automated centrifuges often rotate the harvesting syringes at a rate much higher than needed in order to segregate this type of mixture into its various layers, thus subjecting the tissue to unnecessary manipulation and trauma. Furthermore, since there is no easy, cost-effective way of maintaining the cleanliness of the automated centrifuges (and in particular, the surfaces surrounding the harvesting syringes), the sterility of the environment surrounding the fat tissue is often compromised.

The segregated mixture then needs to be further manipulated in a variety of ways in order to remove the oil and tumescent fluid layers, isolate and clean the fat tissue or fatty layer, and transfer the fat tissue to smaller syringes, e.g., 1 cc syringes, for transplantation. The various manipulation techniques involve rotating the mixture and moving it from one container to another. For example, the harvesting syringe containing the segregated mixture may be flipped around, first to place the tumescent fluid layer on top and decant the tumescent fluid from the mixture, and then to place the oil layer on top and decant the oil from the mixture. The fat tissue may then be injected into another container to be washed, and then injected into the smaller transplantation syringes, so that it may then be injected into the desired location. Each of these manipulations exposes at least some of the mixture and the fat tissue therein to air, in addition to bringing the mixture and tissue into contact with additional instruments and surfaces, and causing other trauma to the tissue. Each exposure to air reduces the viability of the fat tissue, and increases the risk of contamination.

Each manipulation of the mixture, and the fat tissue contained therein, affects the long term results of the transplantation, by comprising the sterility of the tissue and its surrounding environment, and subjecting the tissue to additional unnecessary trauma. The compromised sterility increases the chances of infection, inflammation and rejection of the fat transplant. The unnecessary trauma affects the viability and integrity of the fat tissue, and reduces the durability of the transplant. These effects, together with the high cost of the instruments involved in the process, decrease the desirability of using fat transplants for cosmetic rejuvenation.

SUMMARY

This invention may increase the desirability of using fat transplants for cosmetic rejuvenation by providing a more cost-effective solution for collecting and preparing fat, and improving the long-term results for fat transplantation. The long-term results of fat transplantation are improved by minimizing manipulation of the mixture and the fat tissue contained therein and maximizing the sterility of the mixture, the tissue, and the surrounding environment, at every point during the collection and preparation process, before the fat tissue or fat is injected into the desired location.

This invention may include: a centrifuge; a centrifuge insert which is sterile and replaceable; a syringe with an asymmetrical head at its distal end, and a plunger with a removable plunger shaft and an aspiration port in the plunger head; and an assembly with an adapter having male luer connectors on each end to be coupled with luer ends or luer lock syringes, and a removable filter cap releasably coupleable with the adapter.

In an example embodiment, a mixture of tumescent fluid, fat tissue and oil is first harvested with low vacuum pressure through a cannula into a harvesting syringe. The cannula and plunger shaft are removed from the syringe. The syringe is placed in an insertion cavity in the centrifuge insert. The centrifuge insert is placed on and coupled with the centrifuge. The centrifuge is manually actuated to gently separate or stratify the mixture in the syringe into layers or strata of oil, fat tissue and tumescent fluid with other denser substances. The tumescent fluid and other denser substances are decanted out of the distal end of the syringe through the replaceable filter cap coupled with the adapter, which is coupled with the distal or luer end of the syringe. The filter cap is removed by unscrewing it from the adapter, or if the filter is integrated into the adapter, by breaking off that portion of the adapter containing the filter, leaving an adapter attached to the syringe. The oil is removed from the top of the syringe through an aspiration port in the plunger head in the syringe. The plunger shaft is reattached to the plunger head in the harvesting syringe, and used to push the fat tissue through the adapter into smaller injection syringes, used to inject the fat tissue into the desired locations.

In an example embodiment, a first syringe is mated with a first end of an adapter assembly. A filter assembly is engaged with a second end of the adapter assembly. The filter assembly includes a filter attached to the rest of the filter assembly. The first syringe is inserted into a receiver in a centrifuge insert, such as an insert cavity. A combination of substances is releasably retained inside a chamber of the syringe. The combination includes oil, fat (e.g., fat tissue or cells), and a denser fluid, which may include tumescent fluid and/or other components denser than the fat or oil, e.g., blood, hormones, or other non-fat components which are harvested from the harvesting site along with the fat. The centrifuge insert is coupled with a rotatable centrifuge member of a centrifuge. The first syringe is centrifuged (along with other syringes which may be placed in the centrifuge insert) to stratify the combination into strata of the denser fluid, the fat and the oil. At least a portion of the denser fluid stratum is filtered from the first syringe through the filter. This filtering step may be accomplished, for example, either during or after the centrifuging process. The filter prevents passage of at least a portion of the fat stratum from the first syringe. Additionally, at least a portion of the oil stratum is extracted from an opening in a plunger head in a proximal portion of the syringe. This extraction step may be accomplished, for example, during the centrifuging process, or after the centrifuging process. The filter assembly is disengaged or removed from the adapter assembly, e.g., by unscrewing or breaking off the filter assembly from the adapter assembly, once the denser fluid has been filtered from the first syringe.

In an example embodiment, an assembly includes an adapter and a filter assembly. The adapter has a first section, a second section, a passageway from the first section to the second section, and a coupling. The first section of the adapter is mateable with a luer connector of a first syringe. The second section of the adapter is mateable with a luer connector of a second syringe. The filter assembly is releasably coupleable with the adapter via the coupling. The coupling may be, for example, a threaded engagement or a breakable connection between the adapter and the filter assembly. The filter assembly includes a filter configured to selectively allow passage of a first type of substance out of the first syringe and to prevent passage of a second type of substance out of the first syringe.

In an example embodiment, a first syringe is mated with a first section of an adapter. A first type of substance is then removed from the first syringe through a filter connected to the adapter. The filter prevents passage of a second type of substance from the first syringe. A second syringe is then mated with a second section of the adapter. The second type of substance is then transferred from the first syringe to the second syringe through the adapter.

In an example embodiment, a more dense substance of a combination of substances is removed from a first syringe through a filter attached to an adapter coupled with the first syringe. The filter is configured to permit passage of the more dense substance while preventing passage of a less dense substance from the first syringe. The less dense substance is transferred from the first syringe through the adapter.

In an example embodiment, an assembly includes an adapter and a filter assembly. The adapter has a first end, a second end, a passageway between the first end and the second end, and a coupling. The first end of the adapter is configured to sealingly engage an opening in a first container, such as, e.g., a syringe. The second end of the adapter is configured to sealingly engage an opening in a second container, such as, e.g., another syringe. The coupling may be, for example, a threaded engagement or a breakable connection between the adapter and the filter assembly. The filter assembly is releasably coupleable with the adapter via the coupling. The filter assembly includes a filter configured to selectively allow passage of a first type of substance out of the first container, and to prevent passage of a second type of substance out of the first container.

In an example embodiment, a syringe includes a chamber, a plunger shaft, and a plunger head. The chamber has an open proximal end and an opening in the distal end of the chamber. A center of the opening is offset from a central longitudinal axis of the chamber. The plunger head is releasably coupled with the plunger shaft. The plunger head and the plunger shaft are configured to be slidably and sealingly insertable through the open proximal end into the chamber to variate a volume of an interior of the chamber.

In an example embodiment, a combination of substances in a chamber in a syringe are centrifuged, in order to separate the combination of substances in the chamber into strata according to densities of each of the substances in the combination. A plunger head is slidably and sealingly inserted into an open proximal end of the chamber. The chamber has an opening at the distal end of the chamber. The center of the opening is offset from the central longitudinal axis of the chamber. The plunger shaft is attached to the plunger head after the centrifuging step.

In an example embodiment, an apparatus for centrifuging syringes includes an insert releasably coupleable with a rotatable centrifuge member of a centrifuge. The insert has at least one insert cavity configured to receive a syringe.

In an example embodiment, an assembly for centrifuging syringes includes a centrifuge and an insert. The centrifuge includes a base, and a rotatable centrifuge member rotatably coupled with the base. The insert is releasably coupleable with the rotatable centrifuge member. The insert has at least one insert cavity configured to receive a syringe.

In an example embodiment, a centrifuge insert is coupled with a rotatable centrifuge member of a centrifuge. The centrifuge insert has at least one insert cavity retaining at least one syringe within the insert. The syringe is configured to releasably retain a combination of substances. After the coupling step, the rotatable centrifuge member, the centrifuge insert and the combination of substances is rotated.

In an example embodiment, a mixture of tumescent fluid, fat tissue and oil is first harvested with low vacuum pressure through a cannula into a harvesting syringe. The cannula and plunger shaft are removed from the syringe. The syringe is placed in an insertion cavity in the centrifuge insert. The centrifuge insert is placed on and coupled with the centrifuge. A marking substance (e.g., a dye) is introduced into the syringe and/or the mixture before the centrifuge is actuated: e.g., before or after harvesting or before or after placing the syringe in the insertion cavity, or after the centrifuge insert is coupled with the centrifuge. The centrifuge is manually actuated to gently separate or stratify the mixture in the syringe into layers or strata of oil, fat tissue and tumescent fluid with other denser substances. The tumescent fluid and other denser substances are decanted out of the distal end of the syringe through the replaceable filter cap coupled with the adapter, which is coupled with the distal or luer end of the syringe. The filter cap is removed by unscrewing it from the adapter, or if the filter is integrated into the adapter, by breaking off that portion of the adapter containing the filter, leaving an adapter attached to the syringe. The oil is removed from the top of the syringe through an aspiration port in the plunger head in the syringe. A superficial layer of less viable fat tissue positioned either above or including the marking substance is removed from the top of the syringe through the aspiration port in the plunger head in the syringe. The plunger shaft is reattached to the plunger head in the harvesting syringe, and used to push the remaining more viable fat tissue through the adapter into smaller injection syringes, used to inject the fat tissue into the desired locations.

In an example embodiment, a marking substance comprises a dye that has a density or specific gravity that is higher than or equal to a density or specific gravity of less viable fat tissue. The dye has a color that is designed to visually distinguish a layer of more viable fat tissue in fat in a syringe from a layer of the less viable fat tissue in the fat in the syringe, or otherwise show or highlight the layer of less viable fat tissue, after centrifugation of the syringe and the fat.

In an example embodiment, a dye is introduced into a first type of substance (e.g., fat) or a combination of substances including fat tissue. The substance or combination of substances is releasably retained within a container such as a syringe. The substance or combination of substances are centrifuged or subject to centrifugation in a centrifuge. After being centrifuged, at least a portion of a superficial layer (including, e.g., less viable fat tissue) of the substance or combination of substances is positioned above or includes at least a portion of the dye. At least a portion of the superficial layer is removed from syringe either alone, or together with a portion or all of the dye from the container.

In an example embodiment, a syringe includes a chamber, a plunger shaft, a plunger head and a dye inside the chamber. The chamber has an open proximal end and an opening in a distal end. The plunger head is releasably coupled with the plunger shaft. The plunger head and the plunger shaft are slidably and sealingly insertable through the open proximal end into the chamber to variate a volume of an interior of the chamber.

In an example embodiment, a combination of substances and a dye in a chamber in a syringe are centrifuged, to separate the combination of substances in the chamber into strata according to a density of each of the substances in the combination. A plunger head is slidably and sealingly inserted into an open proximal end of the chamber. The chamber has an opening at its distal end. The center of the opening is offset from a central longitudinal axis of the chamber. After centrifuging, at least a portion of the substances above or including the dye are removed from the chamber, either alone or together with all or a portion of the dye.

In an example embodiment, a marking substance is provided in a syringe in order to provide feedback to an operator on a fat collection and preparation system and process. The marking substance is configured or designed to visually distinguish or separately highlight a layer of less viable fat tissue in fat in the syringe from a layer of more viable fat tissue in fat in the syringe after centrifugation of the fat and the syringe. The syringe, together with the fat and the dye are centrifuged, and then a quantity of the less viable fat tissue or more viable fat tissue in the syringe are measured. A part (e.g., one or more steps or instruments or devices) is adjusted in response to the measurement, in order to maximize a quantity or percentage of more viable fat tissue in a collected and prepared fat sample.

DETAILED DESCRIPTION

The present invention relates to a fat collection and preparation system and method for harvesting fat tissue and preparing harvested tissue for cosmetic rejuvenation and other purposes. FIGS. 1 through 31 illustrate various aspects of the fat collection and preparation system and method according to the present invention.

Figure 1:
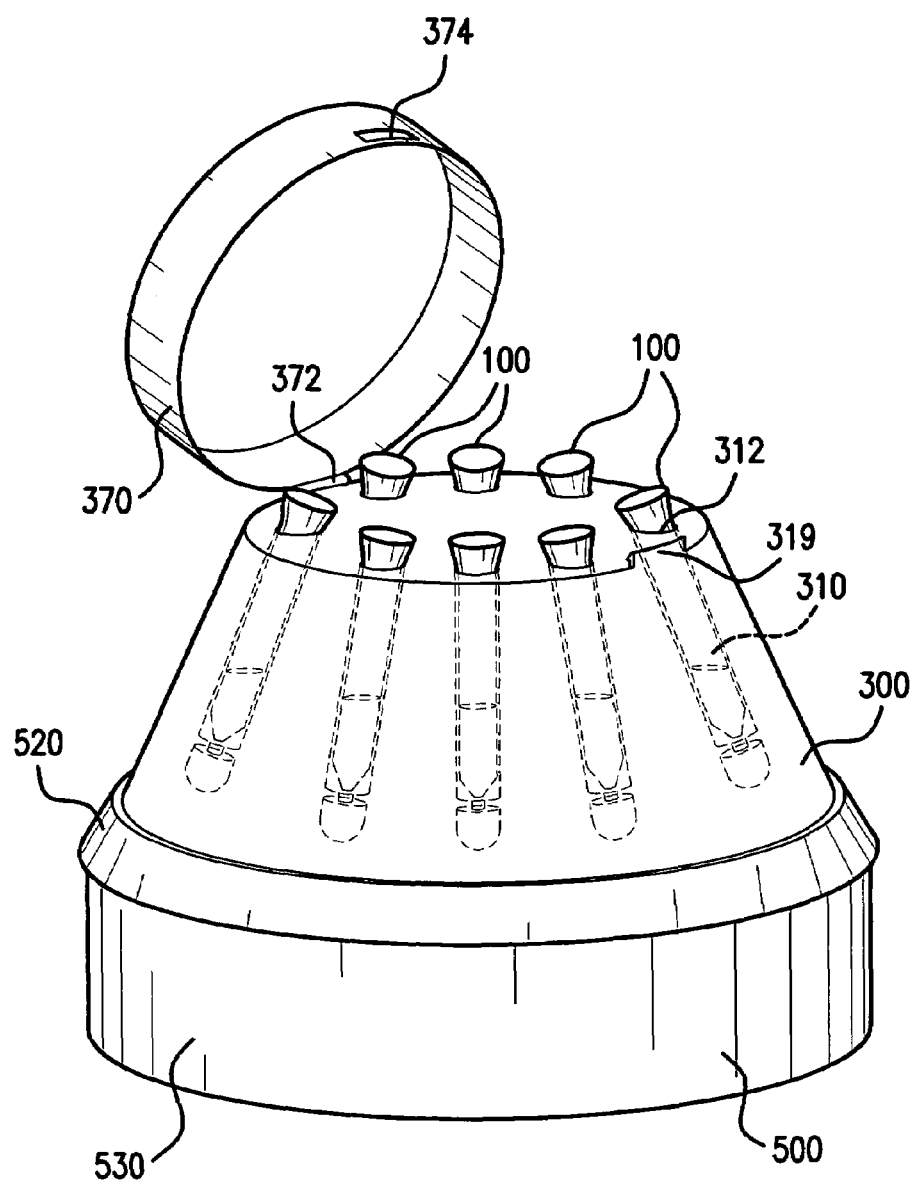
FIG. 1 illustrates a perspective view of an embodiment of a fat collection and preparation system according to the present invention.
Figure 2:
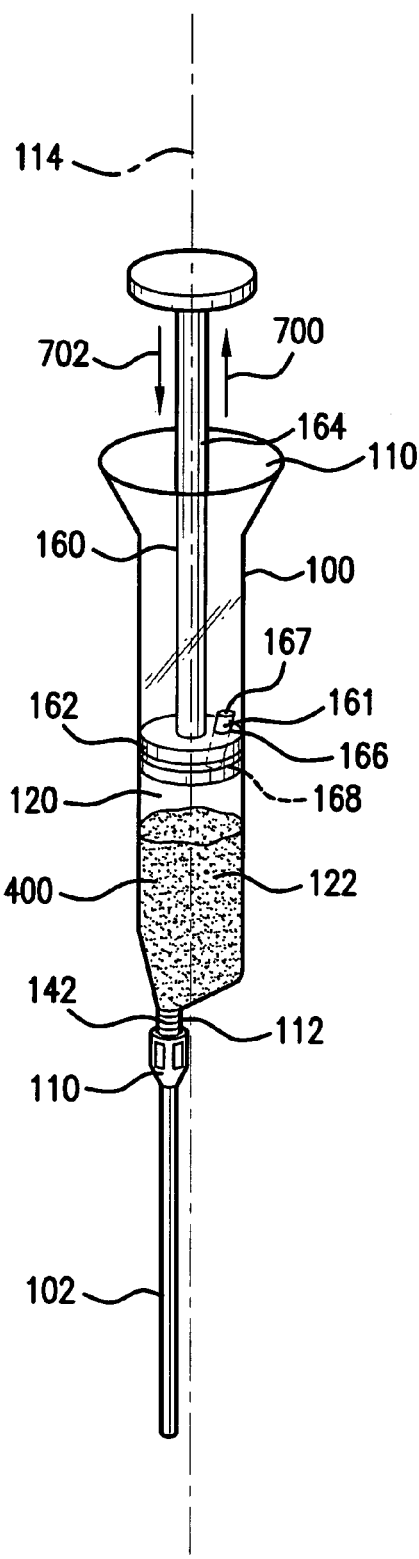
FIG. 2 illustrates a perspective view of a syringe containing a harvested mixture, and having a cannula attached at a distal end of the syringe, of the embodiment of the fat collection and preparation system of FIG. 1.
Figure 6:
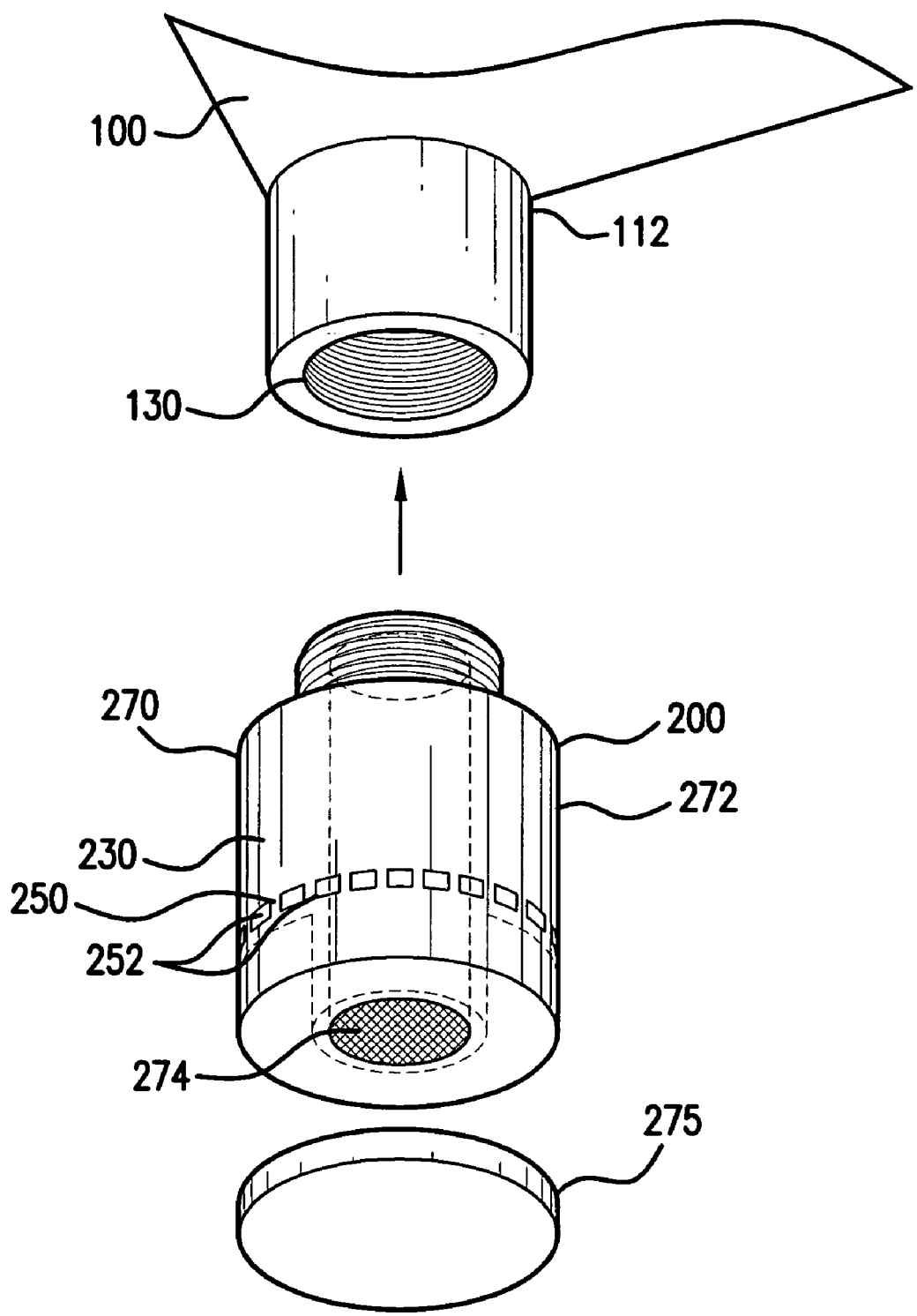
FIG. 6 illustrates an exploded view of an embodiment of an adapter and filter in an embodiment of the fat collection and preparation system.

As illustrated in FIGS. 1 and 2, the system includes syringes 100, an assembly 200, a centrifuge insert 300, and a centrifuge 500. A mixture or combination of substances 400, including oil, fat, tumescent fluid and other denser fluid components, is harvested from a harvesting site, through a cannula 102 into a syringe 100. The syringe 100 is placed or inserted (along with other syringes 100) in the centrifuge insert 300. The syringes 100 are then subject to centrifugation within the centrifuge insert 300, which is coupled with the centrifuge 500. The centrifugation stratifies or separates the mixture or combination of substances 400 into layers or strata according to their densities as illustrated in FIG. 6, including a top or proximal-most stratum 410 of oil 415, a middle stratum 420 of fat 425, including fat cells or fat tissue, and a bottom or distal-most stratum 430 of denser debris or substances 435, including tumescent fluid, connective tissue, hormones and/or other non-fat denser components. Denser substances 435 is drained, filtered, decanted or otherwise removed out of syringe 100 either during or after centrifugation. Oil 415 may be removed through an aspiration valve or port 161 accessing opening 168 in the plunger head 162 of the plunger 160 in the syringe 100. Fat 425 may then be transferred into smaller syringes 600, e.g., 1 cc syringes, for injection in facial wrinkles, depressions, or for other medical purposes. The extracted or removed oil may be discarded or used for other purposes.

Figure 18:
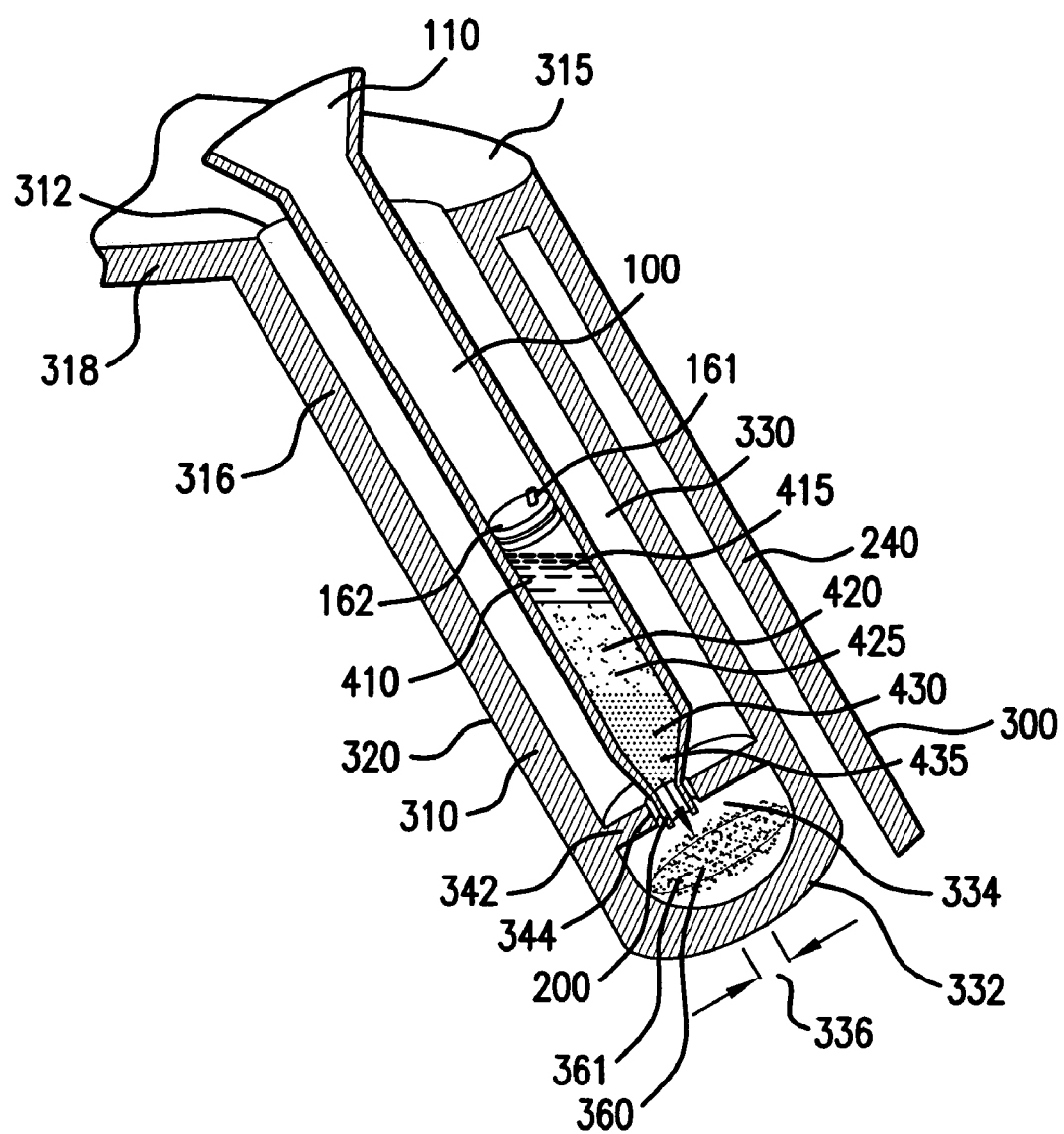
FIG. 18 illustrates a cross-sectional view of the insert, syringe and assembly of FIG. 17, along the line 18-18 of FIG. 17.
Figure 19:
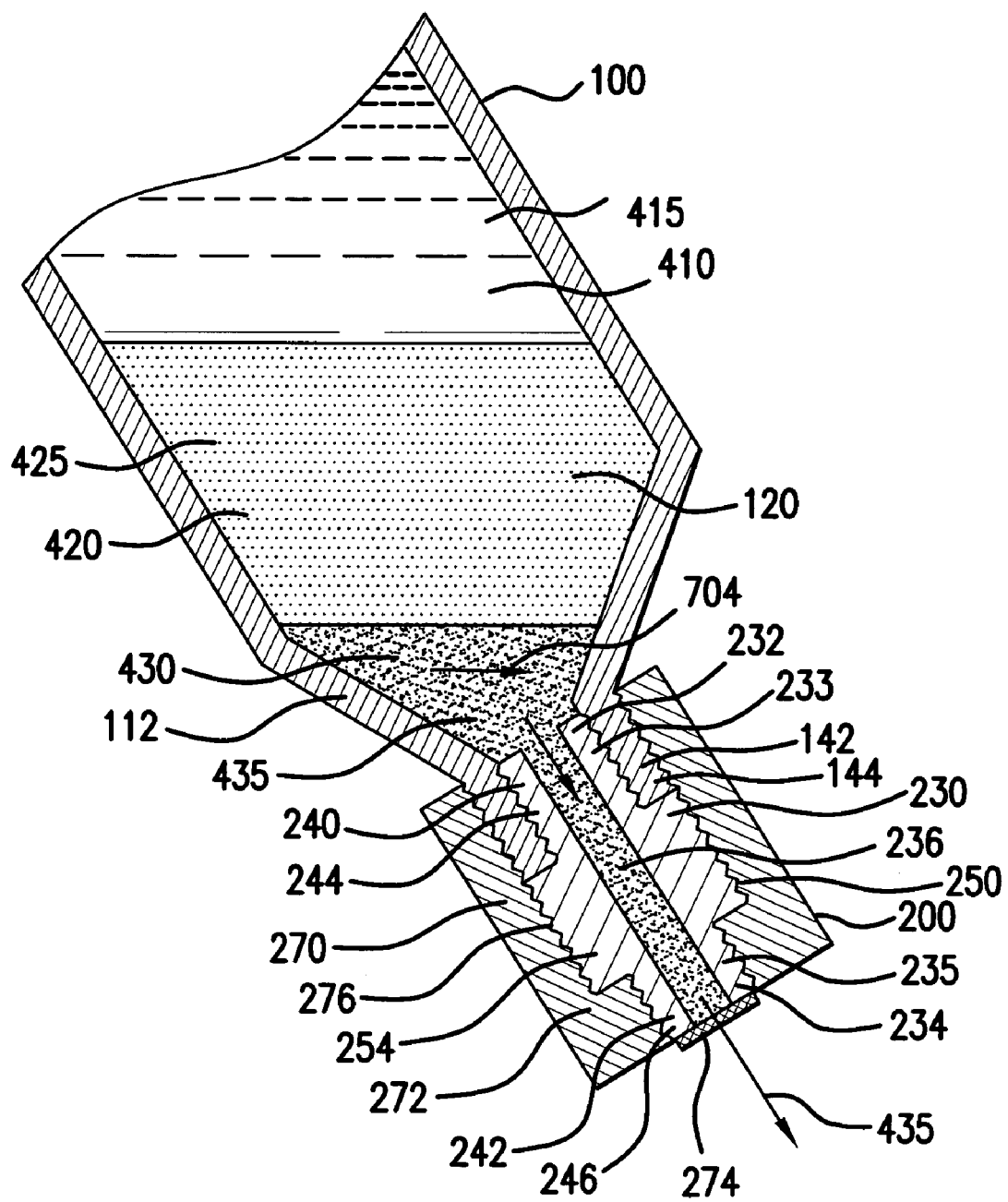
FIG. 19 illustrates a cross-sectional view of the syringe and assembly of FIG. 5 during centrifugation.

The syringe 100 used by an operator for harvesting the mixture or combination of substances 400 from a harvesting site may be designed as illustrated in FIGS. 2 to 4, and FIGS. 18, 19 and 28. The syringe 100 includes a chamber 120 having an opening 130 at its distal or luer end 112, and an open proximal end 110. The opening 130 at the luer end 112 may be positioned off-center or offset from a central longitudinal axis 114 of the syringe 100, so that the opening 130 provides a distal-most outlet when the syringe 100 is positioned at an angle during centrifugation, as illustrated in FIGS. 18 and 19. The offset or off-center position of the opening 130 allows for a larger portion of the denser fluid or substances 415 in the chamber 120 to be drained out of the syringe 100 during centrifugation. In other words, the offset or off-center position of opening 130, allows for the elimination of more of the denser substances 415 including the tumescent fluid from syringe 100 when syringe 100 is in an angled vertical position during centrifugation, without trapping any residual substances or fluid in the chamber 120 of syringe 100.

Figure 16:
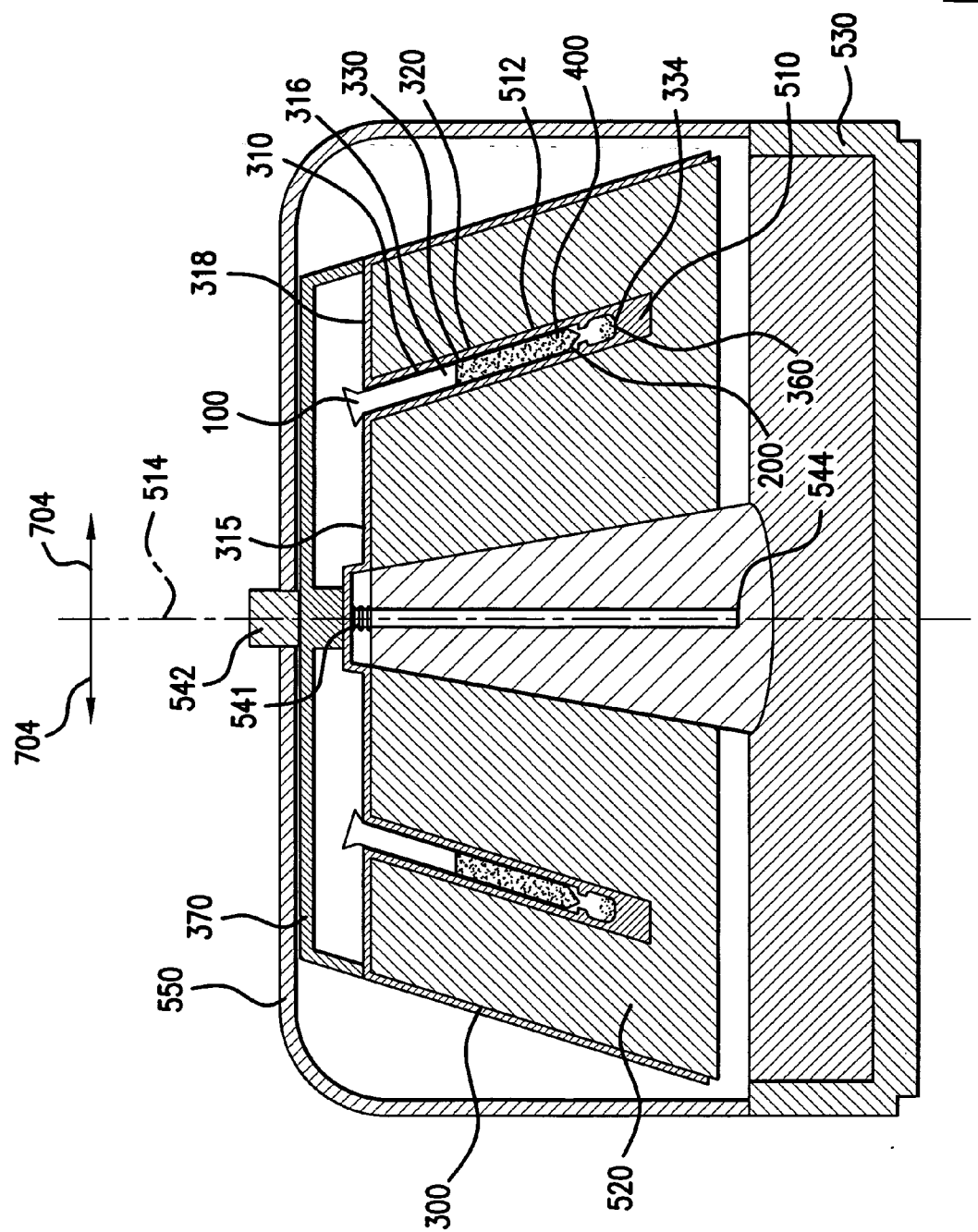
FIG. 16 illustrates a cross-sectional view of the syringes, assemblies, insert and centrifuge of FIG. 9.
Figure 17:
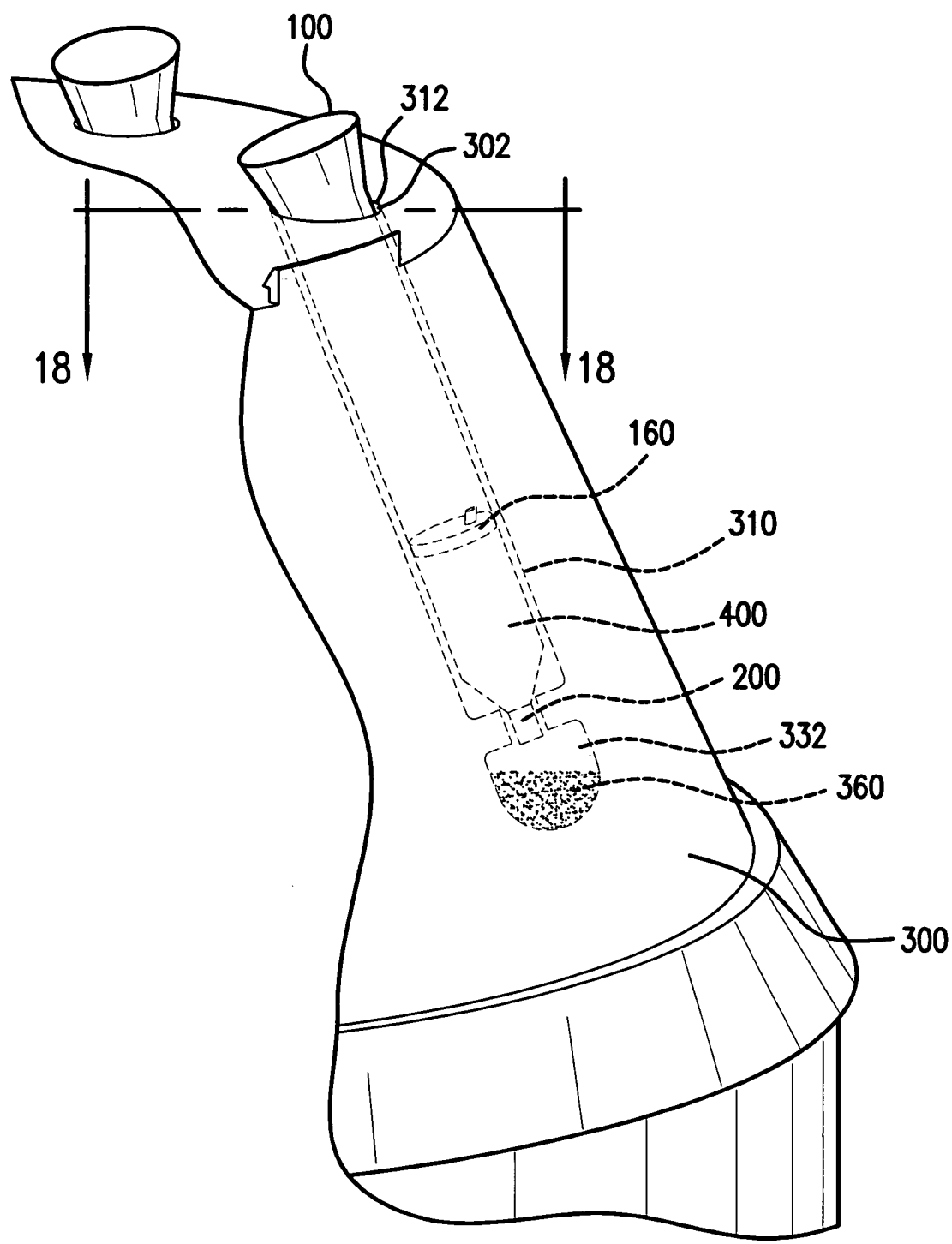
FIG. 17 illustrates a partial perspective view of the insert, syringe and assembly of the embodiment of the fat collection and preparation system of FIG. 1 during centrifugation of the syringes.

The syringe 100 also includes a plunger 160 slidably and sealingly insertable into the open proximal end 110, as illustrated in FIGS. 2 and 3, and FIGS. 28 and 29. The movement of the plunger 160 variates an interior volume 122 of the chamber 120. For example, movement of the plunger 160 in the proximal direction 700, may be used to harvest the substances 400 into the chamber 120, either alone, or with the use of an aspirator. Movement of the plunger 160 in the distal direction 702 decreases the interior volume 122 of the chamber 120, and pushes contents in the chamber 120 out of the syringe 100 through the opening 130. The plunger 160 includes a plunger head 162 and a plunger shaft 164 releasably attached or coupled with the plunger head 162. The plunger shaft 164 may be threadably engaged with the plunger head 162, and removed or unscrewed before the syringe 100 is subject to centrifugation, as illustrated in FIGS. 16 to 18.

Figure 3:
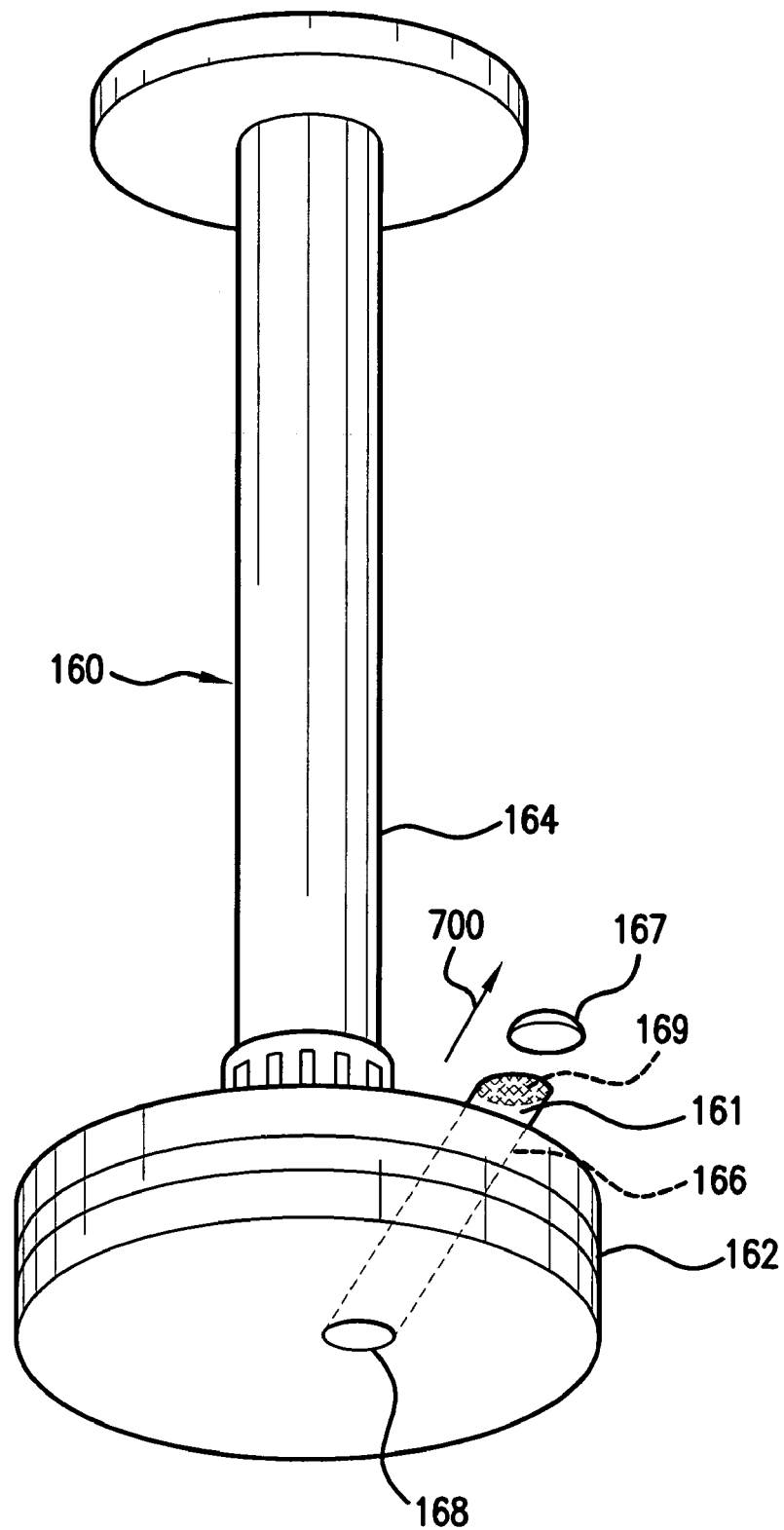
FIG. 3 illustrates a perspective view of a plunger of the syringe of the embodiment of the fat collection and preparation system of FIG. 1.
Figure 28:
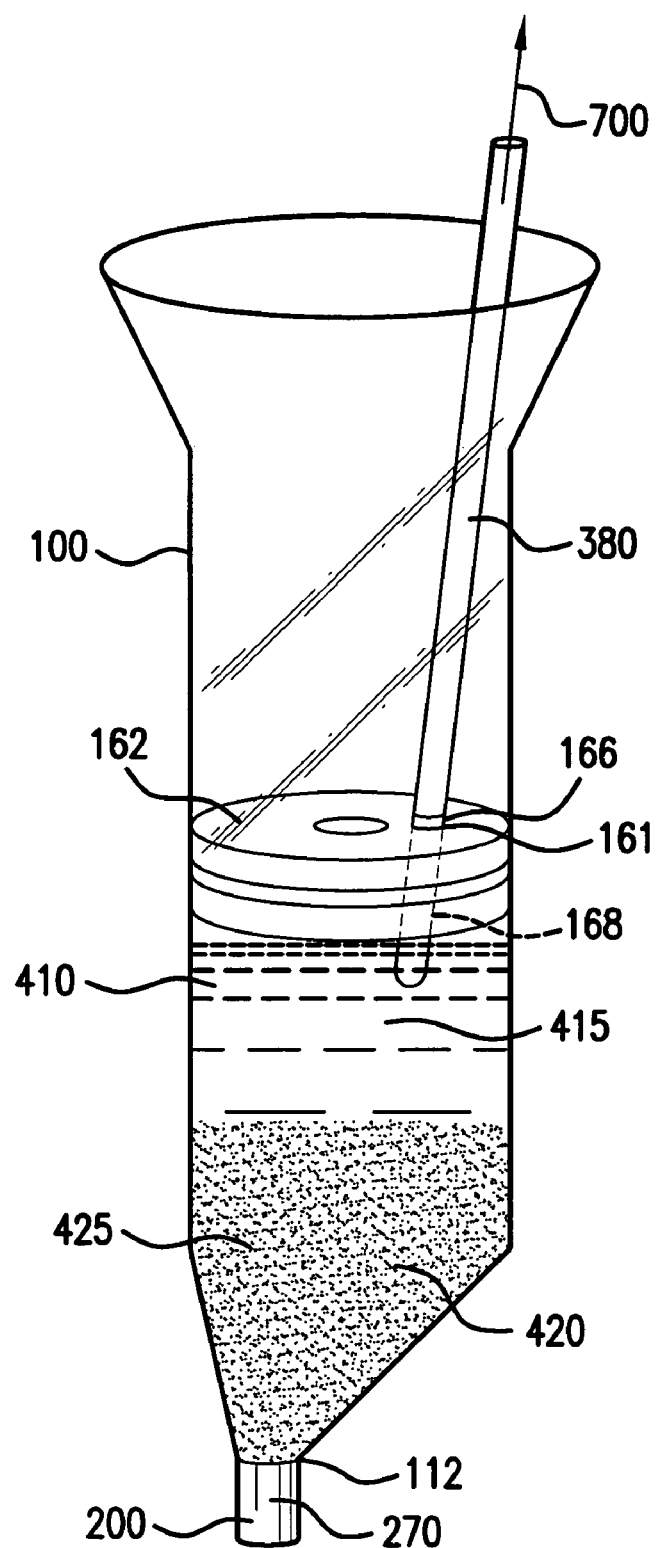
FIG. 28 illustrates a perspective view of removal of oil after centrifugation of the embodiment of the fat collection and preparation system of FIG. 1.

The plunger head 162 may also include a removal device 166 for removing or extracting oil 415 or other substances in a proximal-most stratum 410 from the syringe 100, either during or after centrifugation, as illustrated in FIGS. 2, 3 and 28. The removal device 166 is configured such that, when not in use for removing or extracting oil 415 or other substances from syringe 100, the removal device 166 substantially preserves the sealed enclosure of the interior volume 122. The removal device 166 may include an aspiration valve or a port 161, providing selective access to opening 168. The opening 168 may be positioned off-center or to the side of the plunger shaft 164, as illustrated in FIGS. 2, 3 and 28, or the opening 168 may be positioned such that it is exposed only upon removal of the plunger shaft 164. Regardless of the positioning of the opening 168, the oil 415 or other substances in the proximal-most stratum 410 may be removed or extracted through the opening 168 after centrifugation of the syringe 100 and the substances 400 contained therein.

Alternatively, the removal device 166 may also include a filter 169 covering the aspiration port or valve 161, as illustrated in FIG. 3. The filter 169 permits the oil in the proximal-most stratum 410 to travel in proximal direction 700 out of the syringe 100, during centrifugation, while preventing passage of the fat 425 in the middle stratum 420 from the syringe 100. A closure 167 may be provided to selectively close the opening 168, preserving the enclosure of the chamber 120 while moving the plunger 160 in proximal direction 700 to draw substances 400 into the syringe 100, and while moving the plunger 160 in distal direction 702 to push substances 400 out of the syringe 100, as illustrated in FIGS. 2 and 3.

The luer end 112 of the syringe 100 is configured to accept, and be mated, coupled or otherwise engaged with adapter 230 in assembly 200, as illustrated in FIGS. 4 to 7, and FIG. 29, or to mate or couple the syringe 100 with cannula 102 or other components, devices or assemblies, as illustrated in FIG. 2. The luer end 112 may include a luer locking mechanism 142, such as, for example, a female luer connector 144 configured to receive a male luer connector 244 from adapter 230. The luer end 112 may have internal threads 146 to threadably engage external threads 254 on adapter 230.

Figure 7:
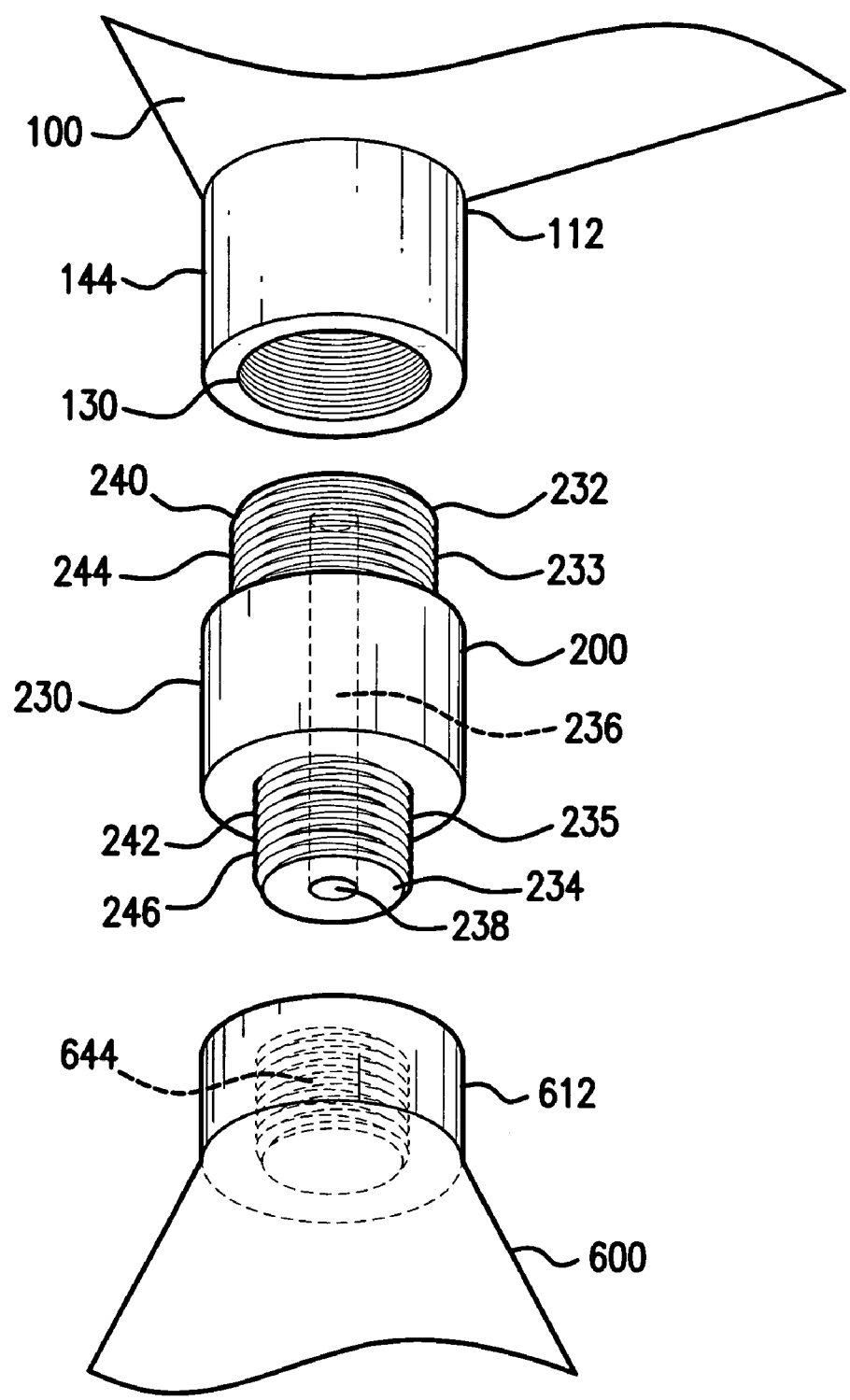
FIG. 7 illustrates an exploded view of an embodiment of the adapter in the assembly, and the syringes of the embodiment of the fat collection and preparation system of FIG. 1.
Figure 29:
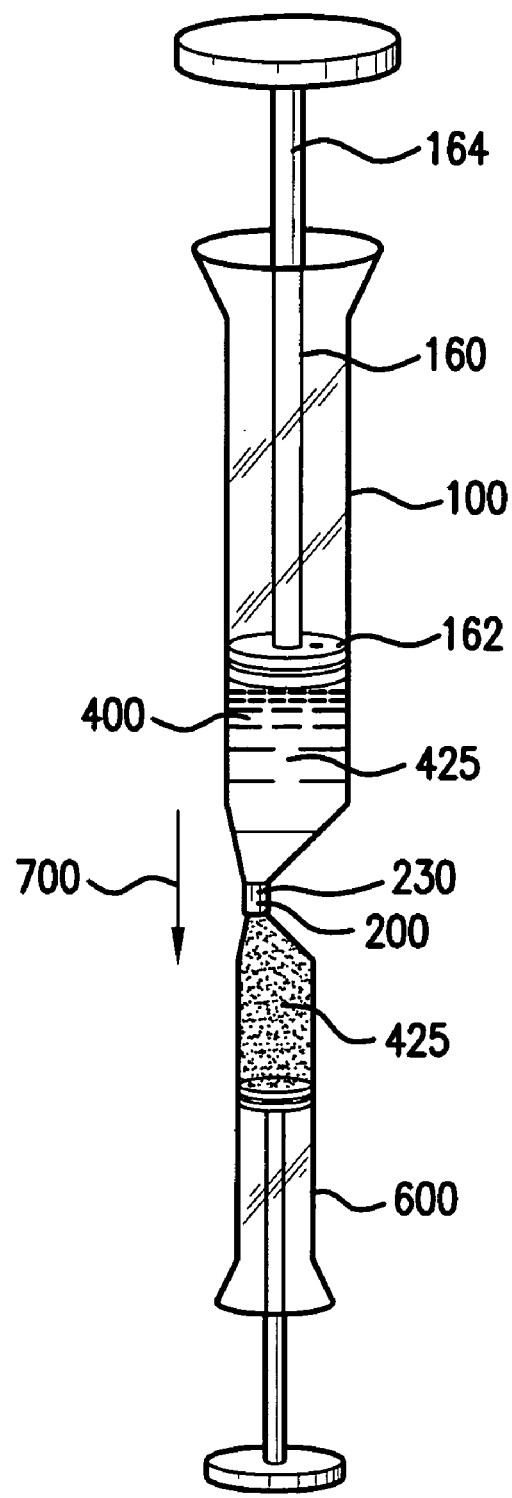
FIG. 29 illustrates a perspective view of transferring fat from one syringe to another syringe through the adapter of the embodiment of the fat collection and preparation system of FIG. 1.

Assembly 200 is configured to be secured, attached, engaged, connected, mated or otherwise coupled with syringe 100, for use during the process of draining, filtering or otherwise removing denser substances 435 in the distal-most stratum 430 from syringe 100, as illustrated in FIGS. 17 to 19. Assembly 200 is also configured for use during the process of transferring fat cells or fat tissue 425 from fat stratum 420 into smaller syringes 600, as illustrated in FIGS. 7 and 29. As illustrated in FIGS. 4 to 7, and FIG. 19, assembly 200 includes adapter 230 and filter assembly 270 releasably coupleable with adapter 230. Adapter 230 has a luer connector 240 at its proximal or first end 232 in its proximal or first section 233, a luer connector 242 in its distal or second end 234 in its distal or second section 235, a passageway 236 from proximal end 232 to distal end 234, and a coupling 250 for releasably coupling filter assembly 270 with adapter 230.

Figure 4:
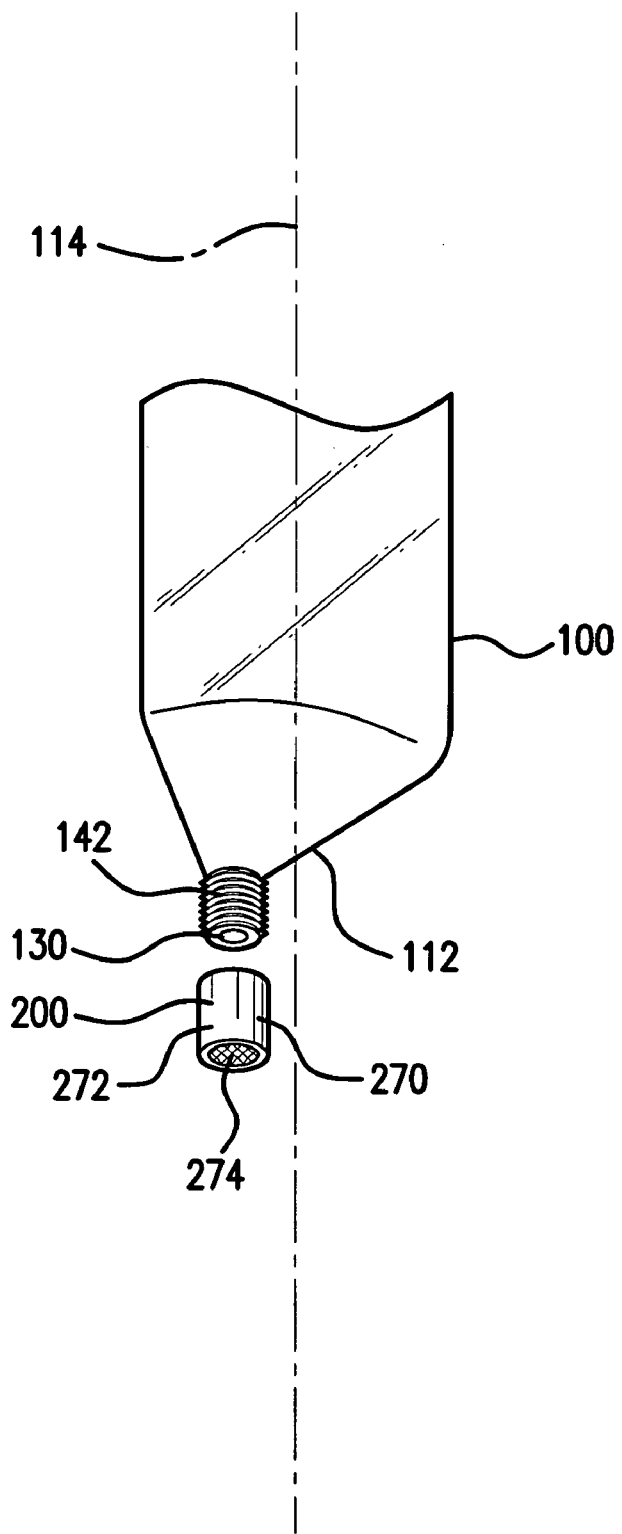
FIG. 4 illustrates a perspective view of an adapter and filter in an assembly of the embodiment of the fat collection and preparation system of FIG. 1.
Figure 5:
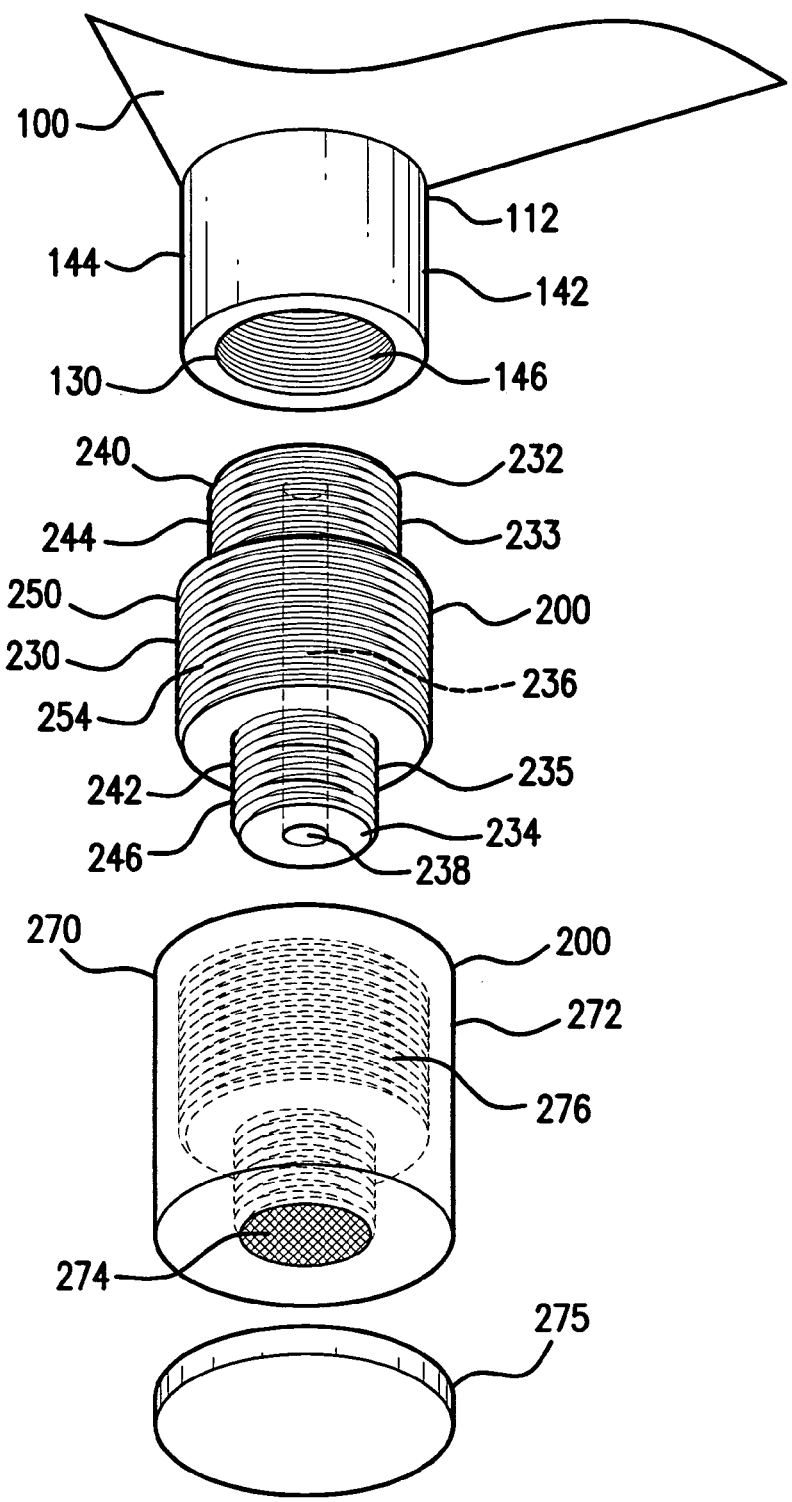
FIG. 5 illustrates an exploded view of an embodiment of the adapter and filter in the assembly of FIG. 3.

Filtering assembly 270 includes filter cap 272 with filter 274, as illustrated in FIGS. 4 to 6. Filter 274 is integrated with filter cap 272, and filter 274 is configured to permit or allow passage of denser substances 435 in the distal-most stratum 430 from syringe 100, while preventing passage of the fat tissue or fat cells 425 in the middle stratum 420 from syringe 100, when syringe 100 is coupled with adapter 230 and adapter 230 is coupled with filter assembly 270, as illustrated in FIG. 19. Once denser substances including tumescent fluid is decanted, filtered, drained or otherwise removed through filter 274, the first fat 425 from the middle stratum 420 touching filter 274 will create an airtight seal protecting the rest of the fat from air contamination. As illustrated in FIGS. 16 through 19, the denser substances may be removed through filter 274 during centrifugation of syringe 100. Alternatively, a cover 275 may be placed over filter 274, as illustrated in FIGS. 5 and 6 before centrifugation and removed after centrifugation, to permit the denser substances 435 in distal-most stratum 430 to be drained or decanted out through filter 274, once syringe 100 is stationary.

Filter 274 may cover opening 238 at distal end 234 of adapter 230, or otherwise be positioned along passageway 236 with a surface area covering a cross section of passageway 236, as illustrated in FIG. 5. Filter cap 272 is configured to accept coupling 250, and releasably engage, connect, couple or mate filter cap 272 to adapter 230, as illustrated in FIGS. 5 and 6. The filter cap 272 may be manufactured together with and attached to adapter 230, with a coupling 250, such as a breakable connector 252, with a capability of being detached after use from the adapter 230, as illustrated in FIG. 6. Alternatively, coupling 250 may include external threads 254 on adapter 230 to be threadably engaged with internal threads 276 in the filter cap 272, e.g., such as a 720-degree threading for strong and secure fit to syringe 100, as illustrated in FIG. 5. Filter cap 274 may be provided as a disposable component, capable of being used with any type of adapter 230 and any type of luer locking mechanism 144 on a syringe 100.

The adapter 230 is coupled with syringe 100 via the luer connector 240, and adapter 230 is coupled with syringe 600 after removing the denser substances 435 from the distal-most stratum 430 via the luer connector 242, as illustrated in FIGS. 7 and 29. Luer connectors 240 and 242 of adapter 230 are releasably coupleable with proximal and distal sections 232 and 234 of adapter 230 with luer ends 112 and 612 of syringes 100 and 600, respectively. A luer connector 240 on adapter 230 such as a male luer connector 244 is configured to couple adapter 230 with luer end 112 of syringe 100, such as a female luer connector 144 of syringe 100. A luer connector 242 such as a male luer connector 246 is configured to couple adapter 230 with luer end 612 of syringe 600, such as a female luer connector 644 of syringe 600. When adapter 230 is coupled with syringes 100 and 600, contents from syringe 100 may be transferred through passageway 236 into syringe 600.

After substances 400 have been harvested from the harvesting site into syringe 100, before centrifugation, and transferring fat from syringe 100 to syringe 600, assembly 200 (including adapter 230 and filter assembly 270 coupled with adapter 230), is coupled with syringe 100, for example, by snapping male luer connector 246 on adapter 230 with female luer connector 144 of syringe 100, as illustrated in FIGS. 4 and 5. The syringe 100 and assembly 200 are then inserted or placed in centrifuge insert 300, as illustrated in FIGS. 1, 16 to 18.

Figure 27:
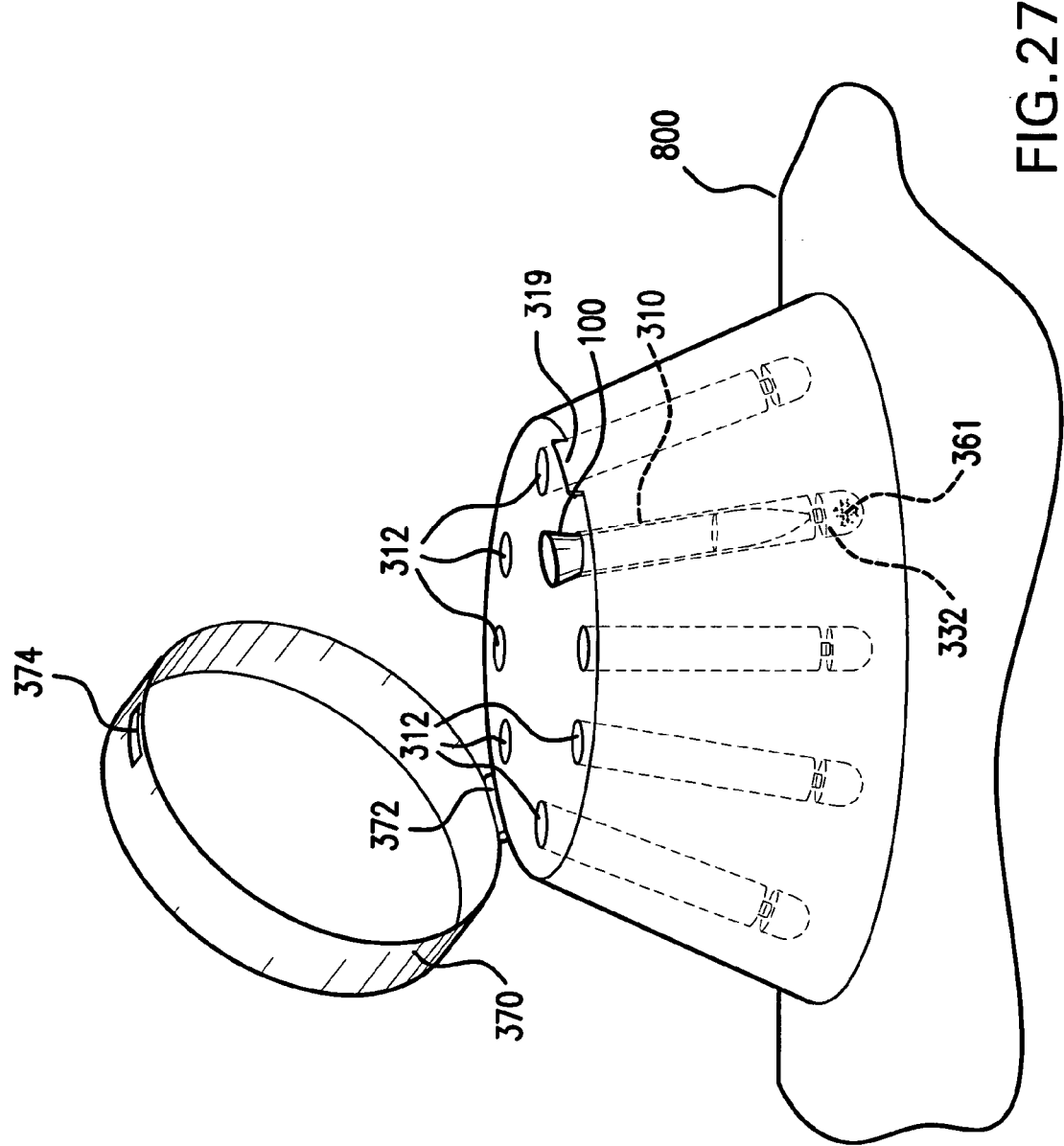
FIG. 27 illustrates a perspective view of the insert and a syringe of the embodiment of the fat collection and preparation system of FIG. 1, which has been removed from the centrifuge and placed on a surface.

Centrifuge insert 300 provides a sterile enclosure or environment for retaining syringes 100 during the centrifugation process in centrifuge 500, as illustrated in FIGS. 1, 8, and FIGS. 14 to 18, and FIG. 27. Centrifuge insert 300 may be molded of plastic, provided as a centrifuge insert mold, and may be disposable after a single use or removable from centrifuge 500 for sterilization before any set of syringes 100 are going to be centrifuged. Centrifuge insert 300 may be made or molded of a plastic material of sufficient rigidity to support syringes 100 after the insert 300 and syringes 100 have been removed from centrifuge 500, in the same angled vertical position as when the syringes 100 and insert 300 are in the centrifuge 500, as illustrated in FIG. 27. Such a sufficiently rigid centrifuge insert 300, in addition to providing a sterile environment for centrifugation, functions as a syringe rack when the insert 300 together with syringes 100 is decoupled and removed from centrifuge 500 and placed or rested on a surface 800.

Figure 14:
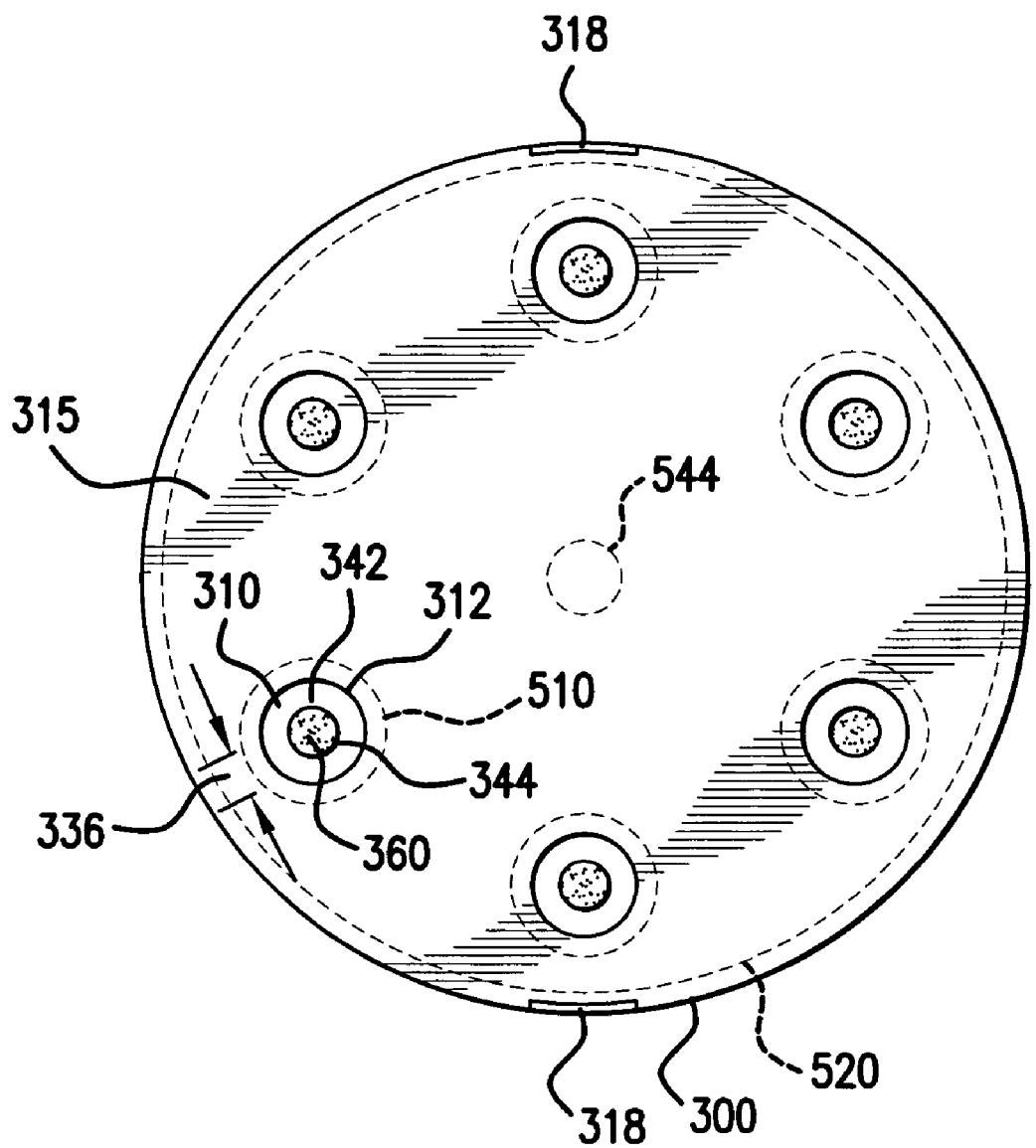
FIG. 14 illustrates a top view of the insert placed on the rotatable centrifuge member of FIG. 13.
Figure 15:
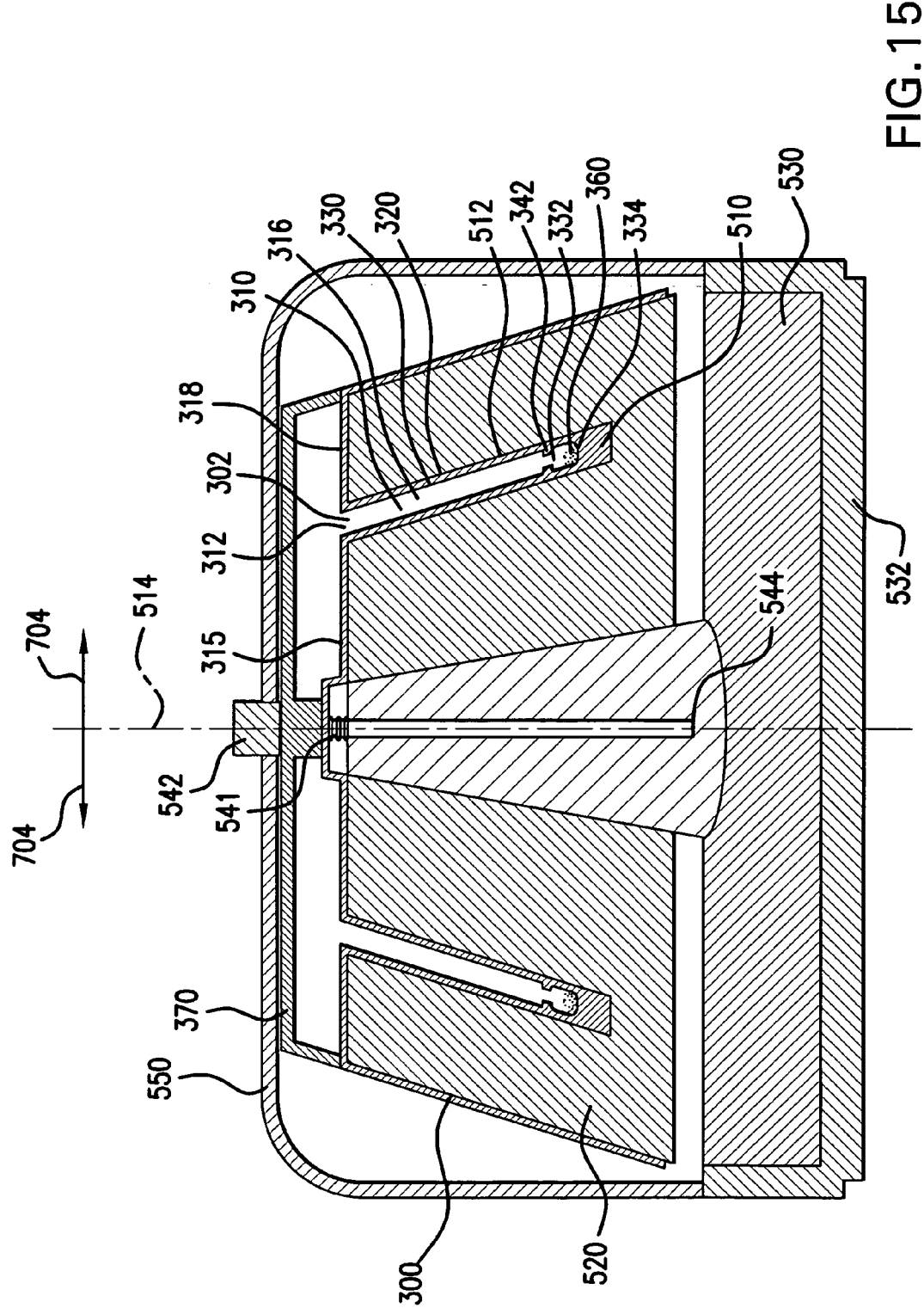
FIG. 15 illustrates a cross-sectional view of the insert and the centrifuge of FIG. 9.

Centrifuge insert 300 has one or more insert cavities 310 configured to receive syringes 100. Insert cavity 310 has an insert port or opening 312 at a proximal end 302 of insert cavity 310 wide enough to receive assembly 200 coupled with syringe 100 and syringe 100. An outer surface 320 may be shaped (or has a shape configured) to provide a complementary fit to an inner surface 512 of a corresponding centrifuge cavity 510 in the rotatable centrifuge member 520 of centrifuge 500 (described further below), as illustrated in FIGS. 14 to 16. The complementary fit of cavities 310 and 510 contributes to securely retaining the syringes 100 within their respective insert cavities 310 during centrifugation, and also contributes to coupling insert 300 with rotatable centrifuge member 520.

An inner surface 330 of insert cavity 310 is shaped to receive at least a portion of a syringe 100 and assembly 200 therein, before centrifugation, as illustrated in FIGS. 1, 8 and 14 to 18, and 27. The inner surface 330 of insert cavity 310 may also have a stop member 342 or stop surface 344 to prevent the luer end 112 of syringe 100 and assembly 200 from resting on a distal-most portion 332 of insert cavity 310. The insert cavity 310 may have a distal segment 334 in the distal-most portion 332 with a smaller cross sectional area 336 than a proximal portion 316 of cavity 310, preventing entry of the assembly 200 and luer end 112 of syringe 100 into the distal segment 334. The distal-most portion 332 may receive the denser substances 435 from the distal-most stratum 430 in syringe 100 through filter 274 in assembly 200 during centrifugation of syringe 100. A quantity of material 360, e.g., an absorbent powder, may be provided or arranged in the distal-most portion 332 to turn the received denser substances into a solid or gel-like substance upon contact adhering to an interior of portion 332. The presence of absorbent material 360 keeps removed denser substances 435 away from the syringe 100 and prevents the removed denser substances 435 from spilling out of the centrifuge insert 300, should the insert 300 be knocked over.

The centrifuge insert 300 also has an insert lid or cover 370 releasably securable or attachable with the insert 300, as illustrated in FIGS. 1, 8, 15 and 27. The insert cover 370 may be integrated with insert 300, or attached to insert 300 with a connector 372, and have a releasable catch 374 engageable with a locking member 319 on insert 300 to enclose the syringes 100 within insert 300 during centrifugation. The insert cover 370 may alternatively or also be threadably engageable with insert 300. Once the cover 370 is closed, the syringes 100 are enclosed within insert 300. This enclosure maintains the sterility of the environment surrounding the syringes 100 by not exposing them to an interior of centrifuge 500 during centrifugation, and preserves the sterility of the surrounding environment when the insert 300 is removed from centrifuge 500. The enclosure also maintains the cleanliness of centrifuge 500.

As illustrated in FIGS. 1, 8 to 16, the centrifuge 500 includes base 530, a rotatable centrifuge member 520 rotatably coupled with base 530, an actuating mechanism 540 coupled with the rotatable centrifuge member 520 to drive a rotation of rotatable centrifuge member 520, and a centrifuge cover 550. The centrifuge cover 550 may be releasably coupleable with the base 530, thus surrounding the rotatable centrifuge member 520, as illustrated in FIGS. 15 and 16. The centrifuge cover 550 may alternatively be releasably coupleable with the rotatable centrifuge member 520. The base 530 may be stationary and have a weighted perimeter 532 to increase the stability of the centrifuge 500 during centrifugation. The centrifuge 500 may be a hand-driven centrifuge 502 or an electrically operated centrifuge 504 (battery operated and/or with an A/C electric cord).

Figure 9:
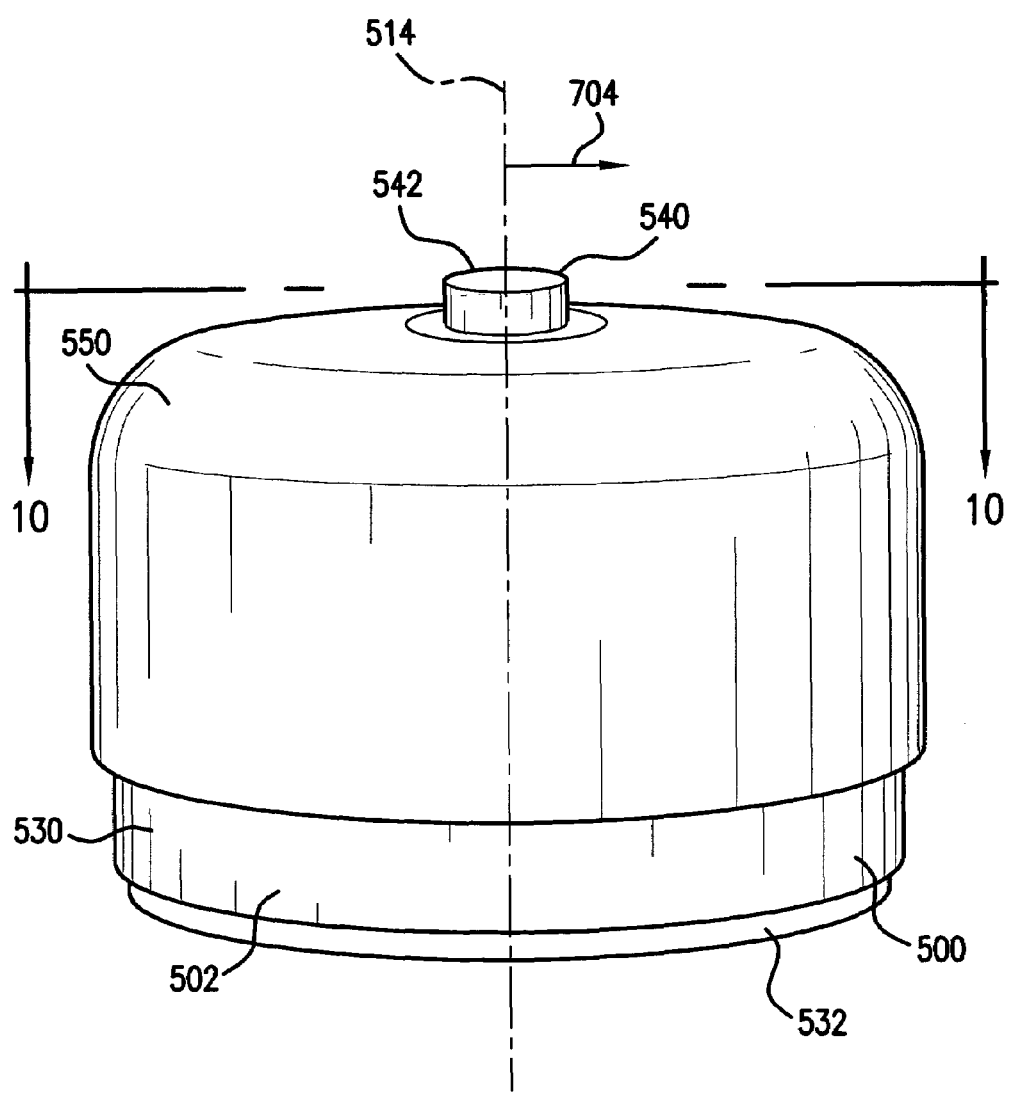
FIG. 9 illustrates a perspective view of a hand-driven centrifuge of the embodiment of the fat collection and preparation system of FIG. 1.
Figure 10:
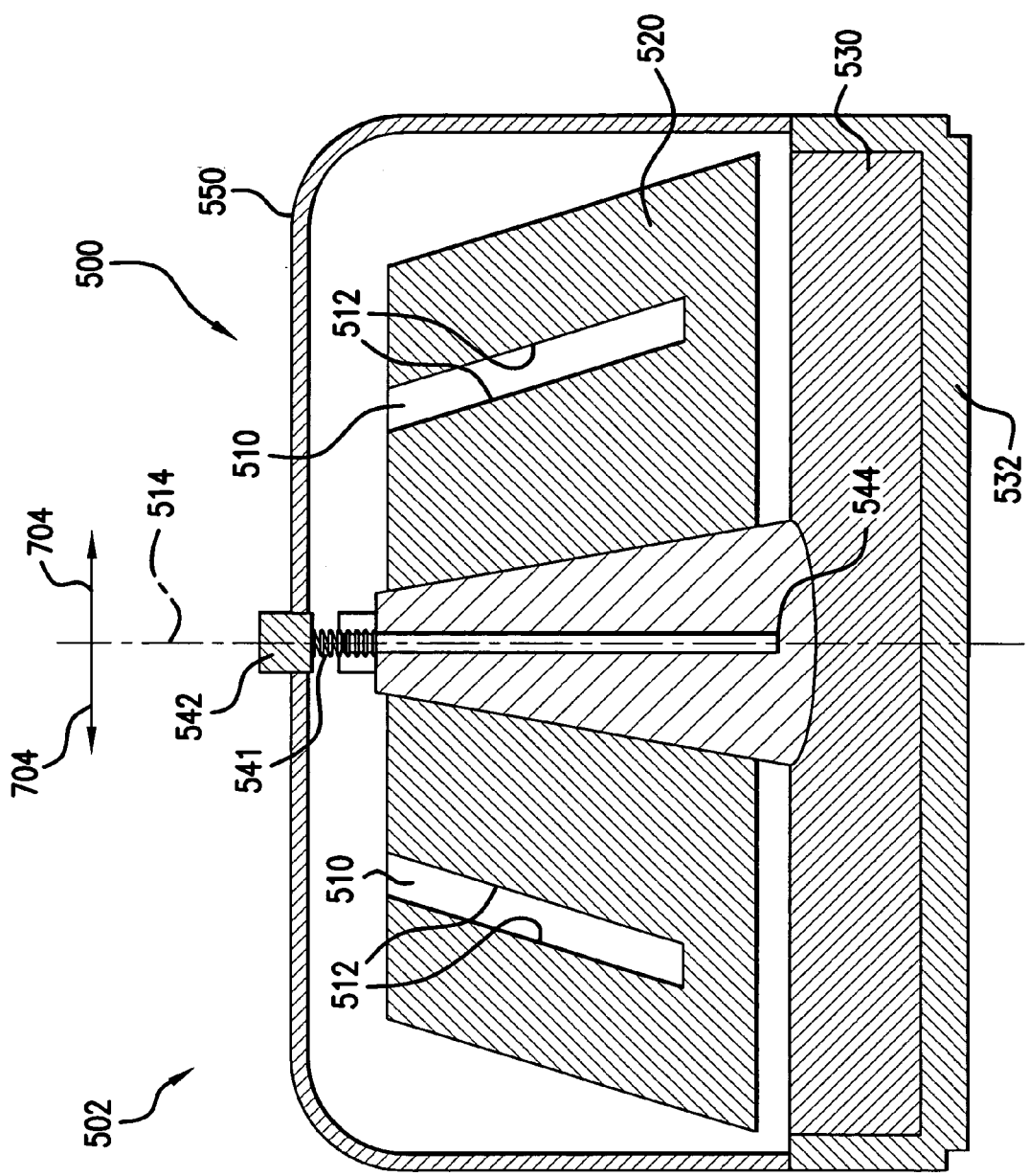
FIG. 10 illustrates a cross-sectional view of the hand-driven centrifuge of FIG. 9, along the line 10-10 of FIG. 9.

In the case of a hand-driven centrifuge 502, as illustrated in FIGS. 9 and 10, the actuating mechanism 540 includes a manually actuated drive shaft 544 coupled with rotatable centrifuge member 520. A button 542 coupled with a spring 541 and the drive shaft 544 may be depressed to actuate rotation of the drive shaft 544, which, in turn, rotates the rotatable centrifuge member 520, and the insert 300 with its syringes 100 and assemblies 200, in order to centrifugate the syringes 100 and substances 400 contained therein. The button 542 may be located on the cover 550, as illustrated, or on the base 530. The button 542 may pumped or pushed three or four times over a three to four minute period to achieve sufficient rotational speed of the rotatable centrifuge member 520 and insert 300. Hand-driven centrifuge 502 may be cost-effective, lightweight and easily transferable to and from an operating suite, together with its contents.

Figure 11:
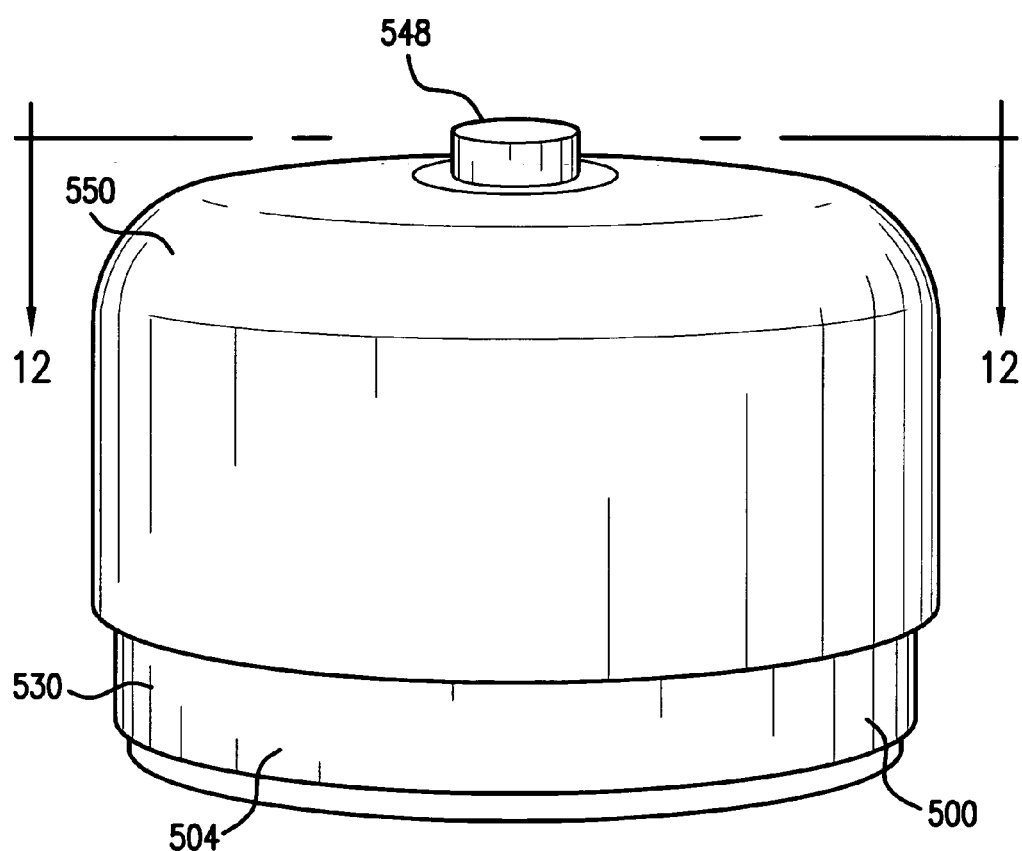
FIG. 11 illustrates a perspective view of an electrically-driven centrifuge of an embodiment of the fat collection and preparation system.
Figure 12:
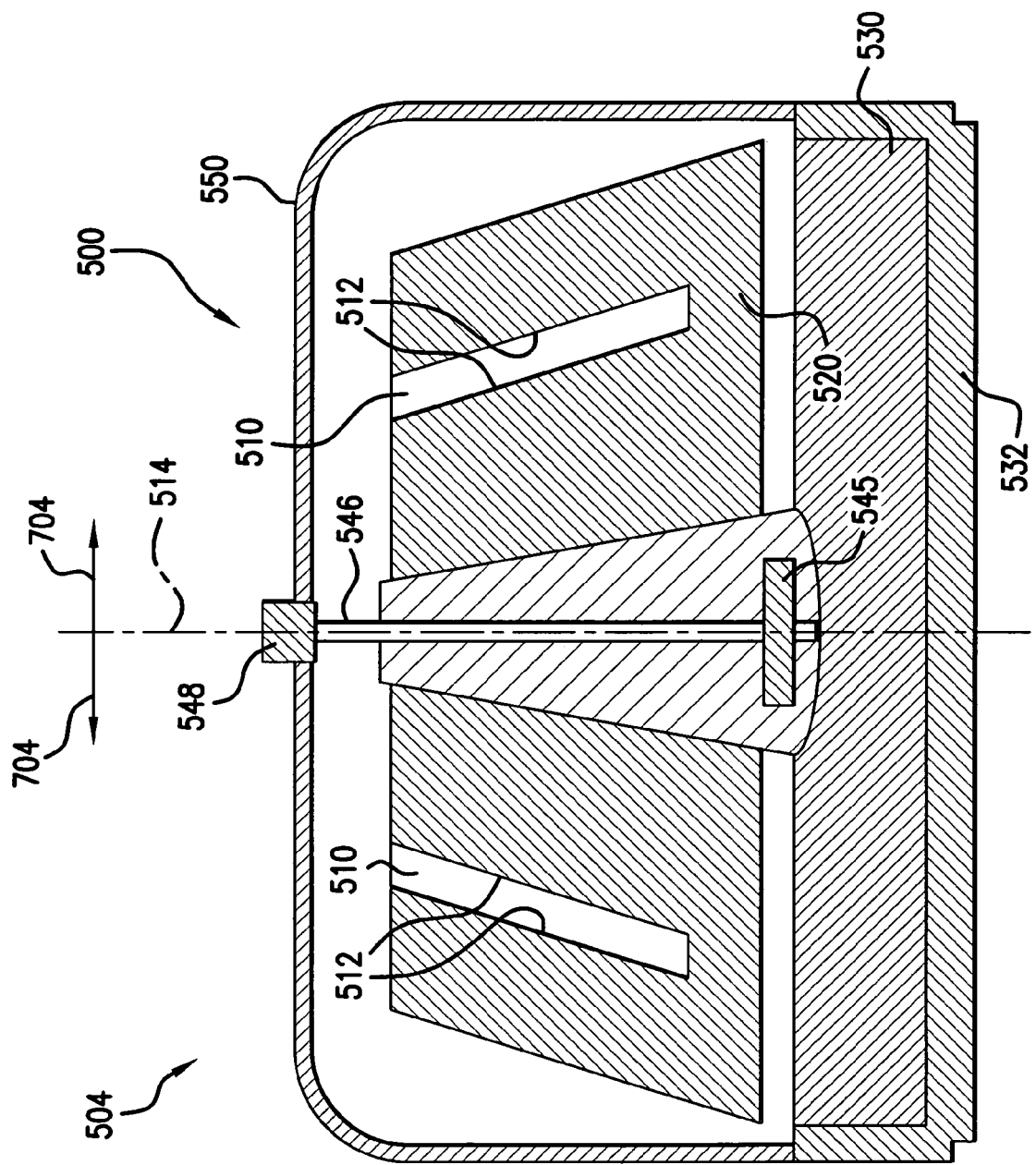
FIG. 12 illustrates a cross-sectional view of the electrically-driven centrifuge of FIG. 11, along the line 11-11 of FIG. 11.
Figure 13:
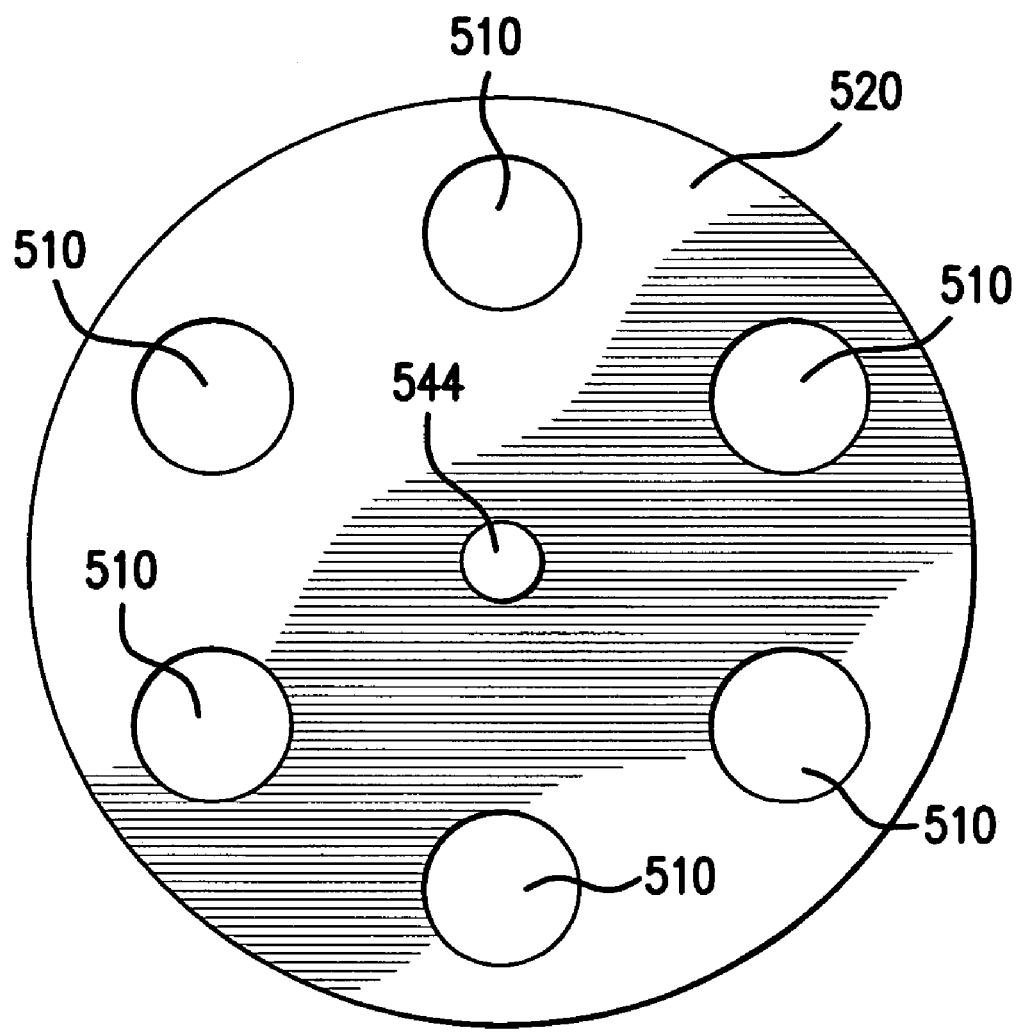
FIG. 13 illustrates a top view of the rotatable centrifuge member of the centrifuge of the embodiment of the fat collection and preparation system of FIG. 1.

Alternatively, as illustrated in FIGS. 11 and 12, the centrifuge 500 may be an electrically operated centrifuge 504 (battery powered and/or powered with an A/C electric cord), in which case, the actuating mechanism includes an electrically driven shaft 546 coupled with rotatable centrifuge member 520. The rotation of the electrically driven shaft 546 is driven by an electric motor 545 which may be actuated or controlled with one or more buttons 548. The button 548 may be located on the cover 550, as illustrated, or on the base 530.

The rotatable centrifuge member 520 has at least one centrifuge cavity 510, as mentioned above. In one embodiment, the rotatable centrifuge member 520 has a plurality of centrifuge cavities 510 which are all substantially the same size, configured to provide a complementary fit for the plurality of insert cavities 310 in centrifuge insert 300, the insert cavities 310 are configured to receive substantially the same sized syringes 100 (together with the assembly 200 on each syringe 100), as illustrated in FIGS. 10, 13 to 16. In such an embodiment, each insert cavity 310 has a matching centrifuge cavity 510.

Figure 23:
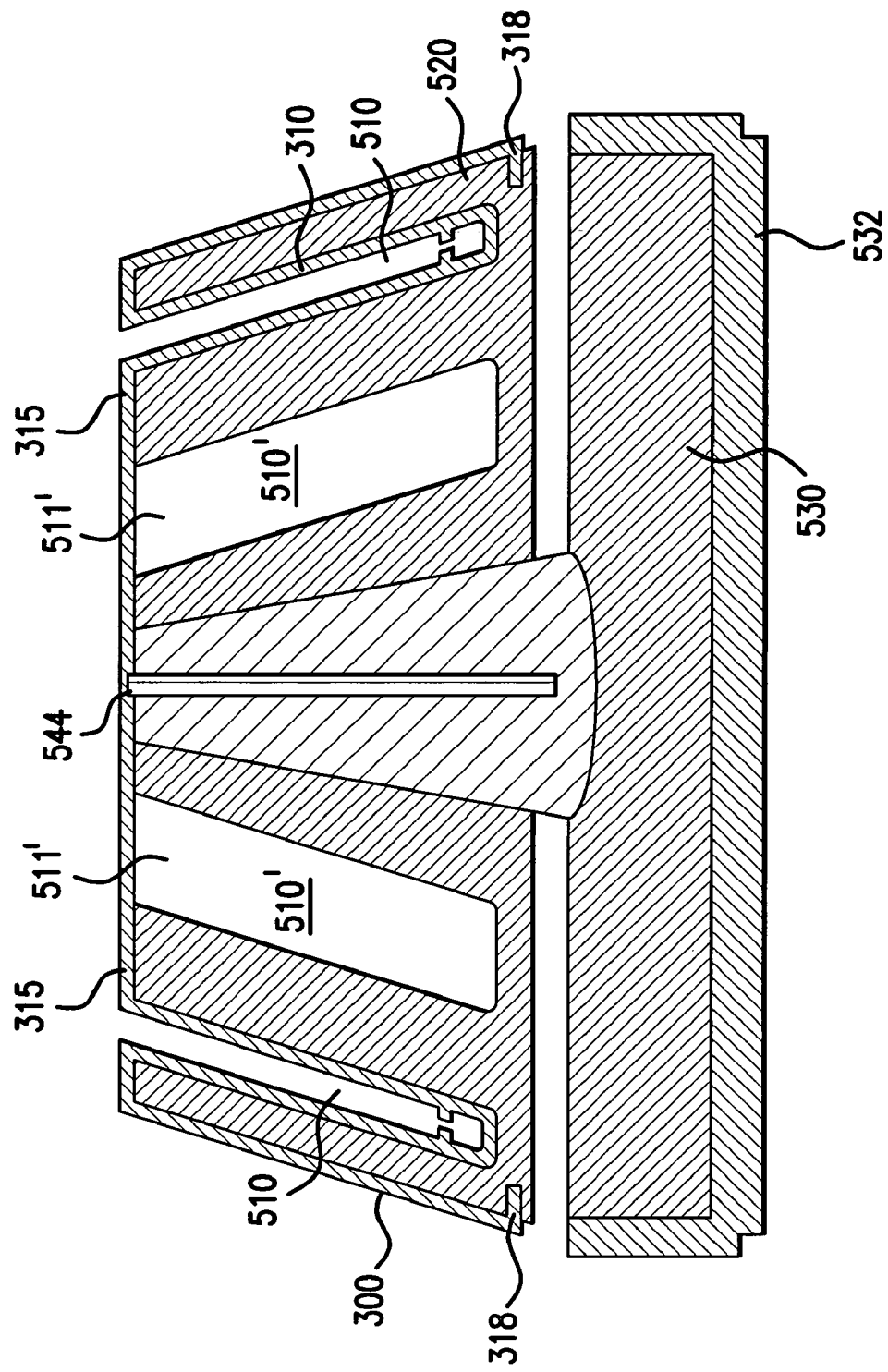
FIG. 23 illustrates a cross-sectional view of an insert, with the rotatable centrifuge member, shaft, and base of the centrifuge of FIG. 21.
Figure 24:
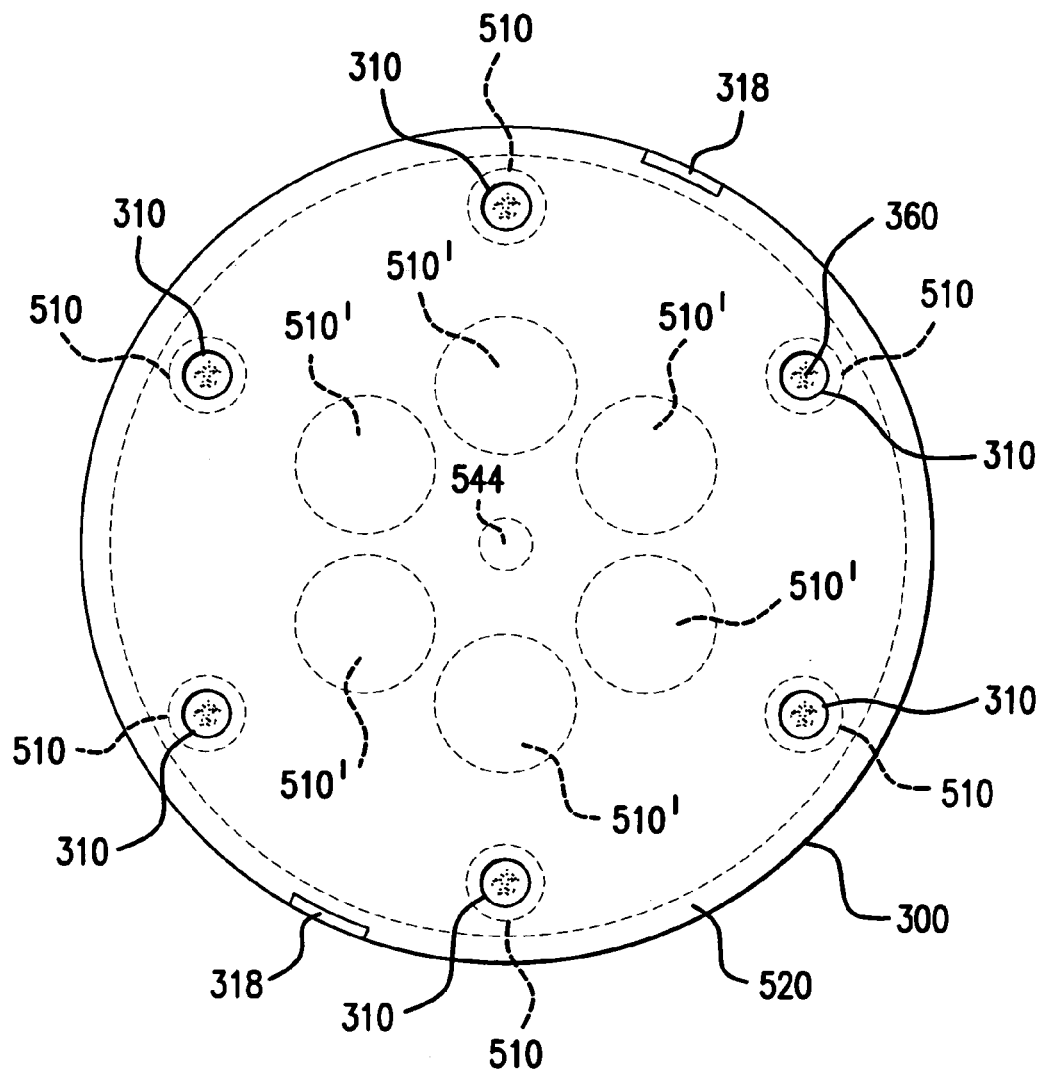
FIG. 24 illustrates a top view of the insert and rotatable centrifuge member of FIG. 23.
Figure 25:
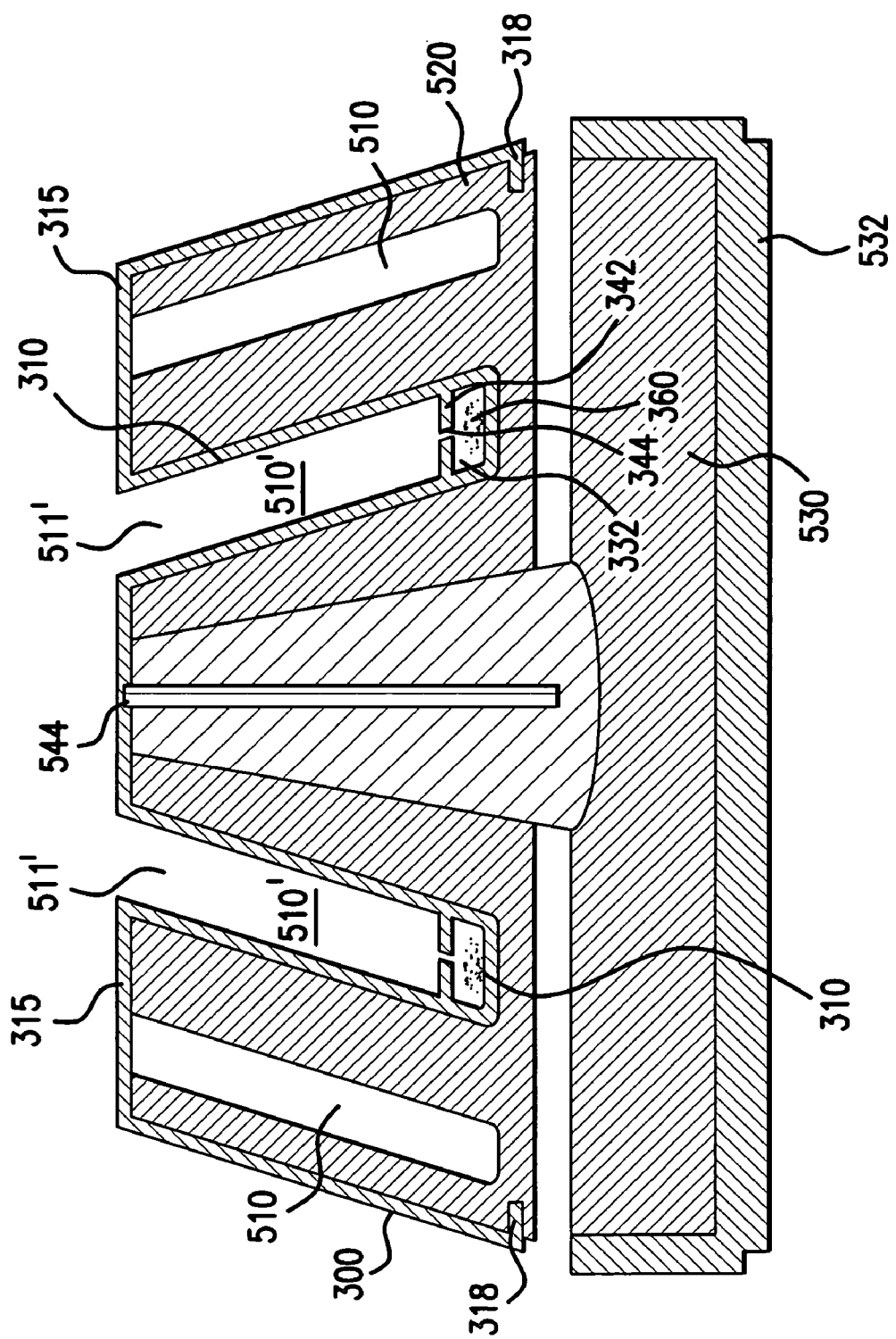
FIG. 25 illustrates a cross-sectional view of an insert, with the rotatable centrifuge member, shaft, and base of the centrifuge of FIG. 21.
Figure 26:
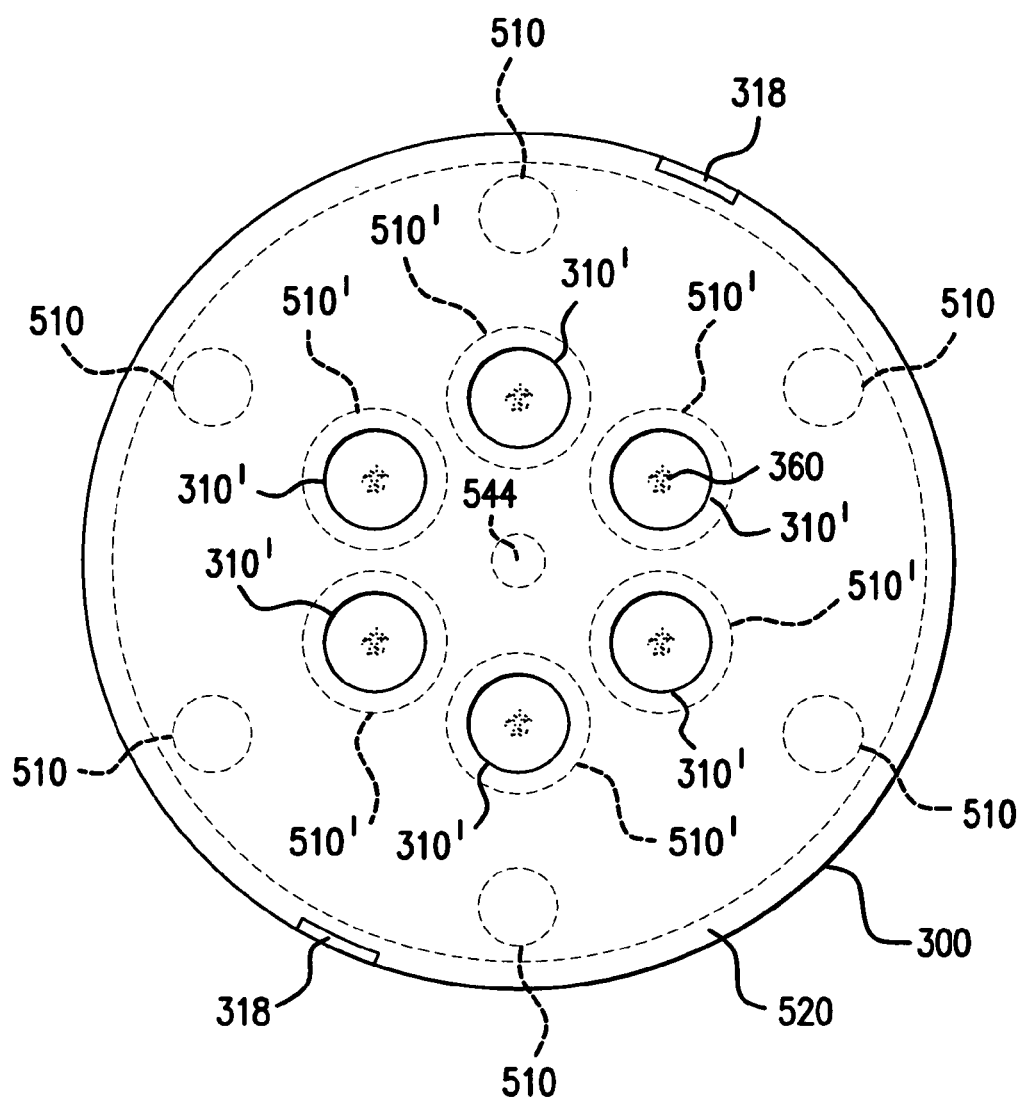
FIG. 26 illustrates a top view of the insert and rotatable centrifuge member of FIG. 25.

In an embodiment, a rotatable centrifuge member 520 may alternatively be designed with differently sized centrifuge cavities 510 for accommodating differently sized insert cavities 210 and syringes 100 (together with the assembly 200 on each syringe 100), e.g., 10 cc syringes in one centrifugation and 20 cc syringes in another centrifugation, as illustrated in FIGS. 21 to 26. In this other embodiment, a centrifuge insert 300 has insert cavities 310 dimensioned to receive at least a portion of particularly sized syringes 100, e.g., 10 cc syringes, and their respective assemblies 200. The insert cavities 310 have matching or corresponding centrifuge cavities 510 dimensioned for the insert cavities 310 and the 10 cc syringes 100 and assemblies 200. The rotatable centrifuge member 520 also has larger centrifuge cavities 510' dimensioned for accommodating larger insert cavities, e.g., for 20 cc syringes. Such larger centrifuge cavities 510', and their open ends 511' are covered by a proximal surface 315 of centrifuge insert 300, as illustrated in FIGS. 23 and 24. Another centrifuge insert 300 may be provided for another centrifugation with insert cavities 310' which are configured to fit only the larger centrifuge cavities 510' and leave the smaller centrifuge cavities 510 unmatched and covered by the proximal surface 315 of the insert 300, as illustrated in FIGS. 25 and 26.

In either embodiment, the complementary fit of the insert cavities 310 and centrifuge cavities 510 provides, as described above, a coupling to couple the insert 300 with the rotatable centrifuge member 520, as illustrated in FIGS. 14 to 16, and 23 to 26. Insert 300 may have other additional mechanisms or components or members 318 to connect, engage, mate, secure or otherwise couple insert 300 with rotatable centrifuge member 520, as illustrated in FIGS. 14, and 23 to 26. Once insert 300 is coupled with rotatable centrifuge member 520, rotation of the rotatable centrifuge member 520 drives a rotation of the insert 300. Insert 300 rotates with the rotatable member 520 during centrifugation.

Figure 20:
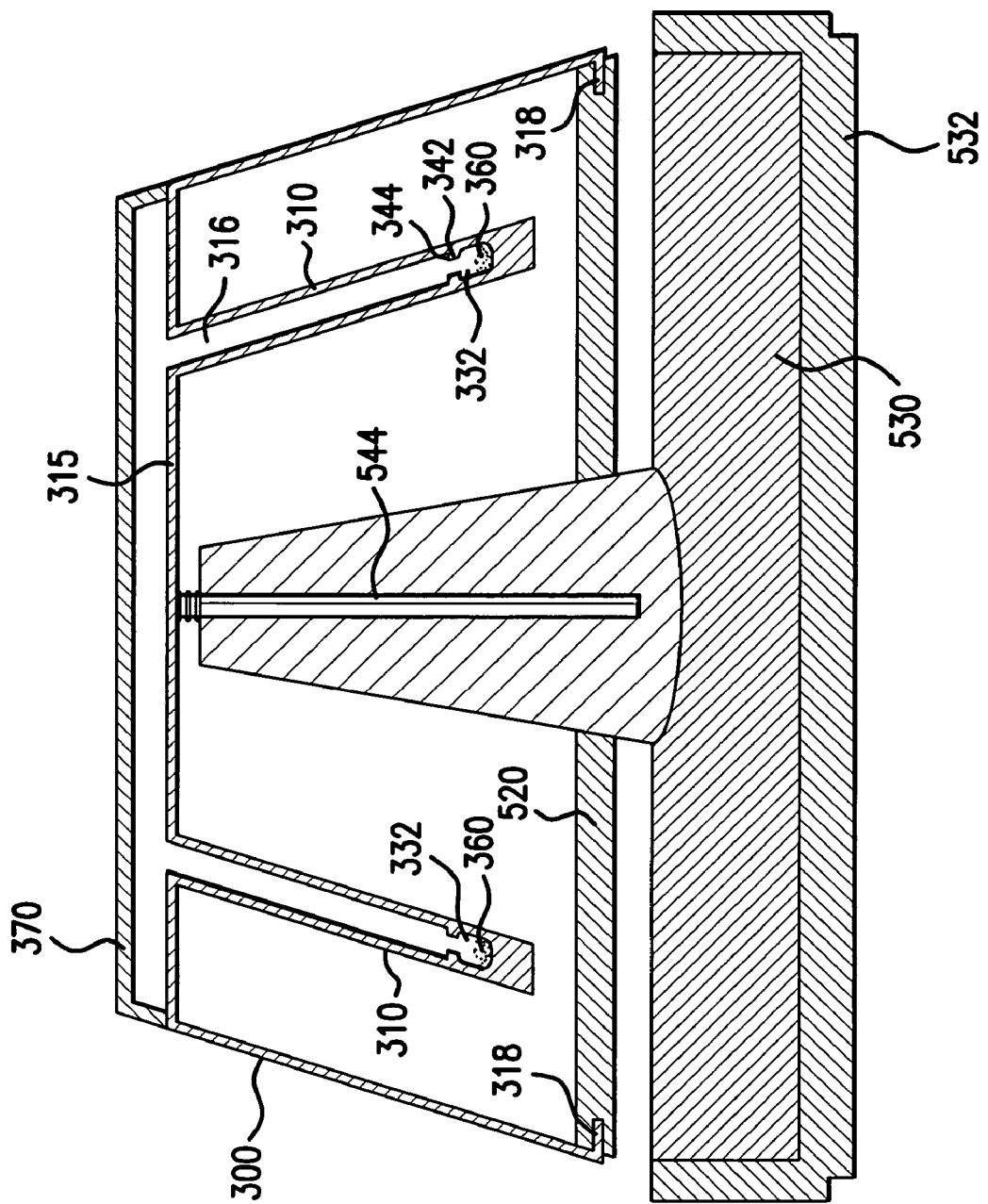
FIG. 20 illustrates a cross-sectional view of an insert, rotatable centrifuge member, shaft, and base of a centrifuge of an embodiment of the fat collection and preparation system.
Figure 21:
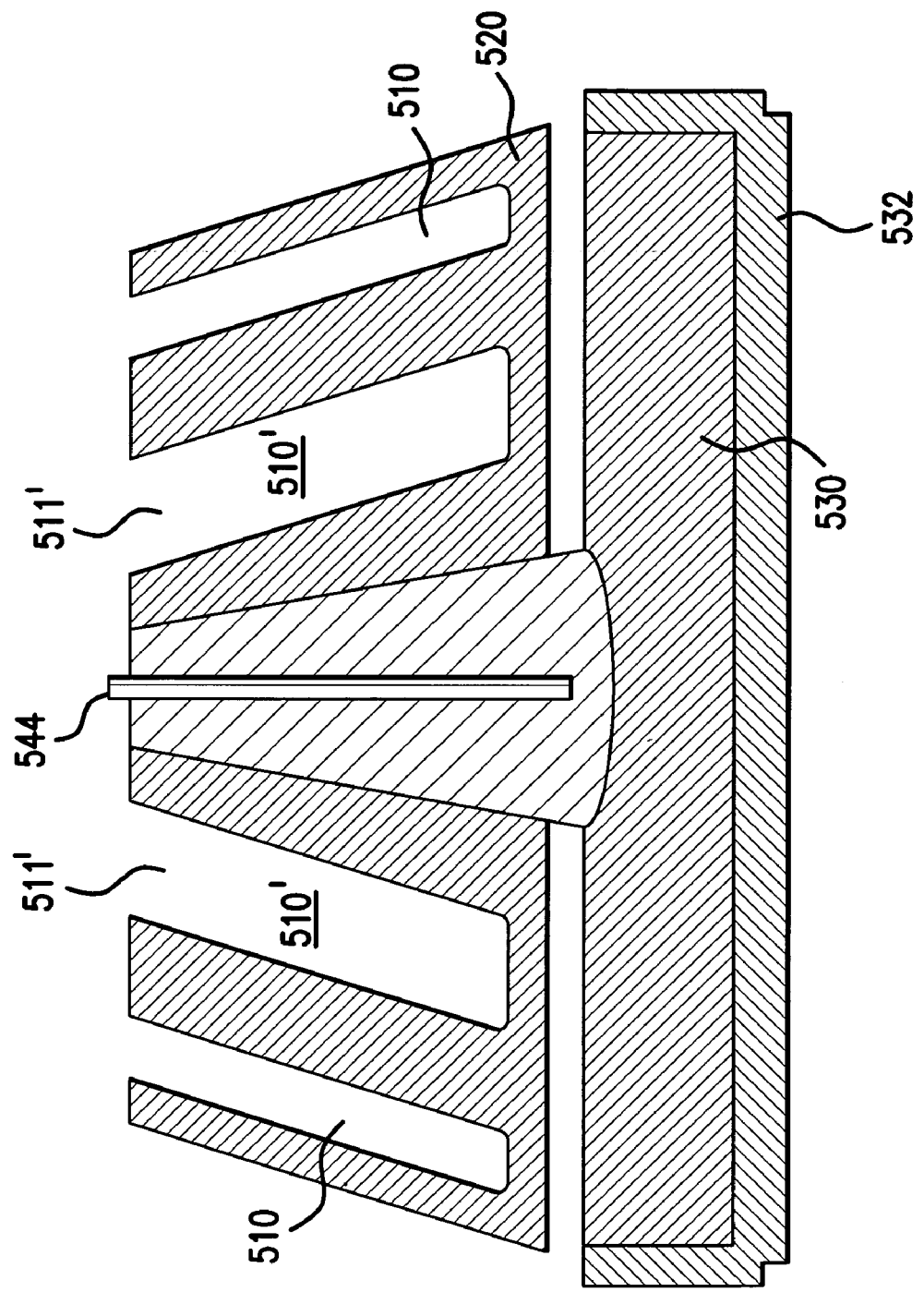
FIG. 21 illustrates a cross-sectional view of a rotatable centrifuge member, shaft, and base of a centrifuge of an embodiment of the fat collection and preparation system.
Figure 22:
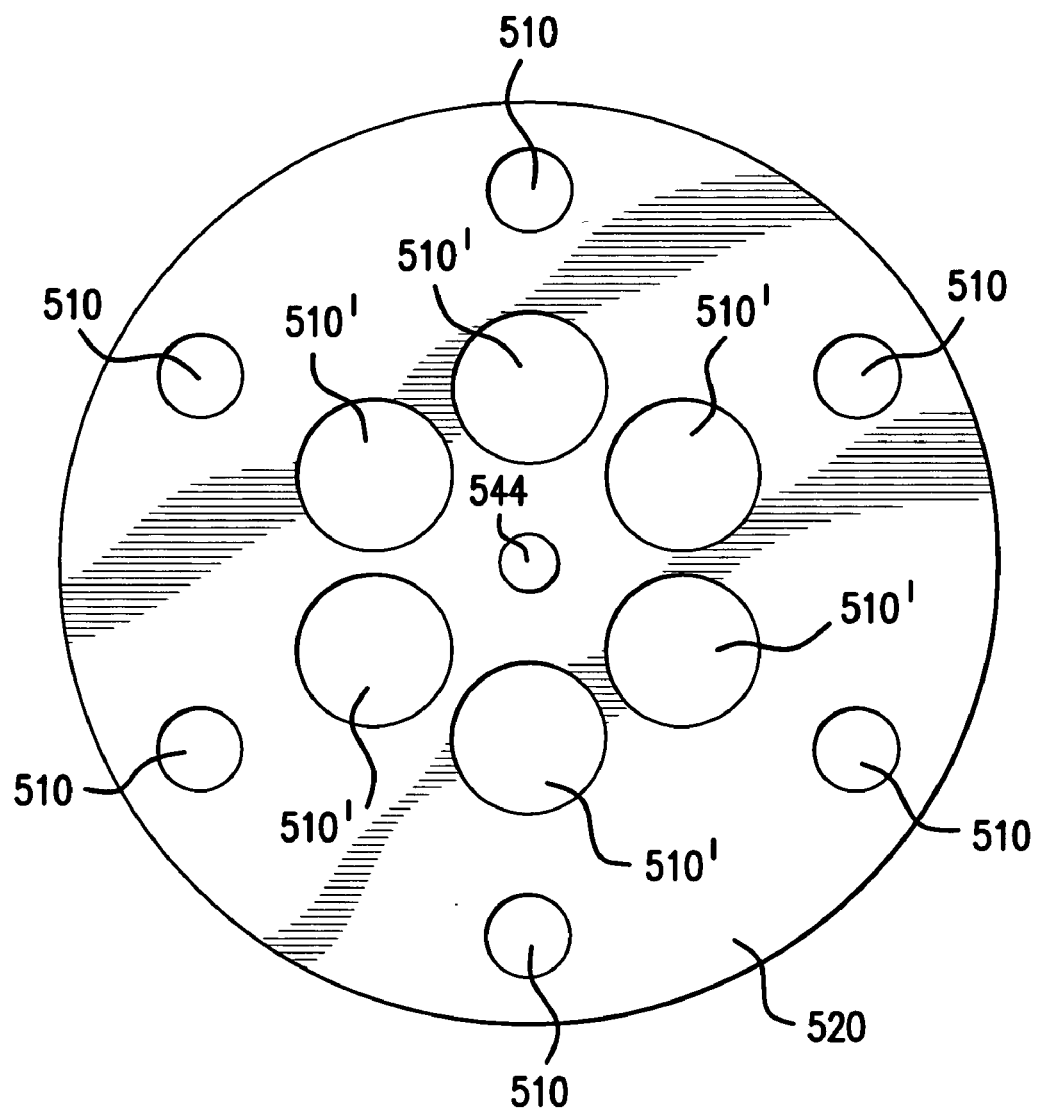
FIG. 22 illustrates a top view of the rotatable centrifuge member of FIG. 21.

In an embodiment illustrated in FIG. 20, the rotatable centrifuge member 520 need not have any centrifuge cavities 510, provided that rotatable centrifuge member 520 has another mechanism, component or member to couple the insert 300 with rotatable centrifuge member 520, and the insert 300 is sufficiently rigid and securely maintains the syringes 100 in their respective insertion cavities 110 during centrifugation.

In operation, various combinations of the embodiments of the syringe 100, assembly 200, centrifuge insert 300, and centrifuge 500 may be used together with the methods described below to collect and prepare fat 425 for transplantation, with minimal manipulation of syringes 100 and the fat 425.

After a fat harvesting site is injected with tumescent fluid, the combination or mixture of substances 400, including oil 415, fat 425 (such as fat tissue or fat cells), and tumescent fluid and other denser substances 435 are harvested through a cannula 102 connected with syringe 100, into chamber 120 of syringe 100, as illustrated in FIG. 2. The substances 400 may be harvested by aspirating the substance 400 from the harvesting site, and/or by pulling the plunger 160 in proximal direction 700 to draw the substances up through cannula 102 into chamber 120 of syringe 100. The cannula 102 is then removed from syringe 100.

An assembly 200 is then coupled with each such syringe 100, as illustrated in FIGS. 4 to 6, and 19. Specifically, a luer connector 240 of adapter 230 may engage a luer connector 142 of syringe 100, coupling the adapter 230 with syringe 100. The filter cap 272 is coupled with adapter 230 by threadably engaging the adapter 230, or the filter cap 272 may be manufactured or provided already coupled with the adapter 230 in assembly 200.

The centrifuge insert 300 is coupled with the rotatable centrifuge member 520, as illustrated in FIGS. 8, 14, 15 and 20. The insert cavities 310 are inserted into matching or corresponding centrifuge cavities 510 in rotatable centrifuge member 520, and a small portion of absorbent material 360 is provided in the distal-most portion 332 of each insert cavity 310, as illustrated in FIGS. 14 and 15.

Figure 8:
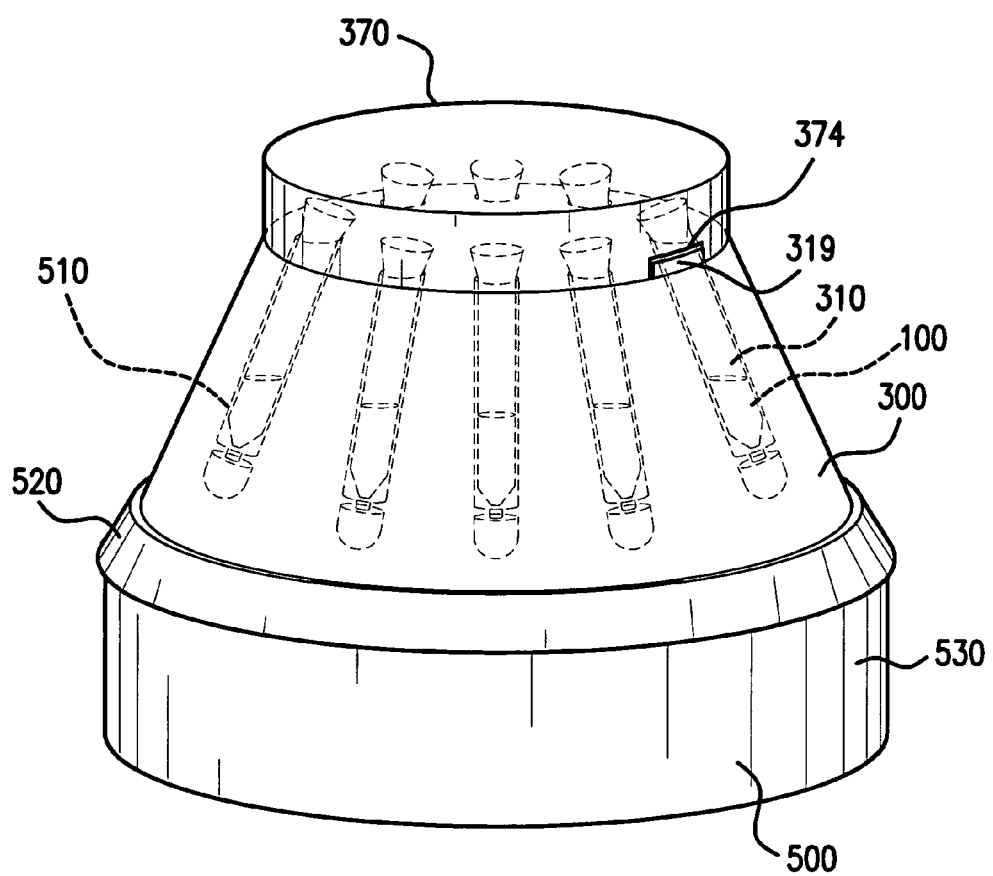
FIG. 8 illustrates a perspective view of the insert and centrifuge of the embodiment of the fat collection and preparation system of FIG. 1.

The syringes 100, together with their respective assemblies 200, are placed or inserted, at least in partially, into insert cavities 310 in centrifuge insert 300, as illustrated in FIGS. 1, 17 and 18. The cover 370 of the centrifuge insert 300 is closed, to enclose the syringes 100, their respective assemblies 200 and substances 400 within the insert 300, as illustrated in FIG. 8. The centrifuge 500 is then closed by placing cover 550 over the rotatable member 520 and secured or coupled with base 530, as illustrated in FIGS. 9 and 16.

The syringes 100, substances 400 and assemblies 200 are then subject to centrifugation or centrifuged in the centrifuge 500, as illustrated in FIGS. 16 to 19. Centrifugation may be accomplished by periodically depressing button 542 to actuate the spring 541 and rotate or otherwise spin the drive shaft 544 and the rotatable centrifuge member 520 for a hand-driven centrifuge 502, or by adjusting button 548 to adjust the speed of the motor 545 rotating the drive shaft 546 and the rotatable centrifuge member 520 for an electrically operated centrifuge 504, illustrated in FIGS. 9 to 12. Rotatable centrifuge member 520 should be rotated at a sufficient rotational speed for a sufficient duration to: stratify the substances into separate oil stratum 410, fat stratum 420 and denser substances stratum 430 (strata according to the densities of the substances 400), as illustrated in FIGS. 18 and 19 while minimizing the structural damage to the fat cells or tissue 425 in the fat stratum 420 during centrifugation. For example, centrifuge 500 may be operated at a speed ranging from 500 to 1000 rpm, for approximately 2 to 4 minutes.

The denser substances 435 in stratum 430 are decanted, drained, filtered, eliminated or otherwise removed from syringe 100 through filter 274 either during or after centrifugation. The denser substances 435 may be removed during centrifugation, provided that assemblies 200 including filter caps 272 are coupled with the syringes 100 before centrifugation and the filter 274 is not covered during centrifugation, as illustrated in FIGS. 16 to 19. The removed denser substances 435 may pass through filter 274, into the distal-most portion 332 of insert cavity 310. Rotation of syringe 100 provides a force acting radially outward 704 from a central vertical axis 514 of centrifuge 500, leading the denser substances 435 to travel, forming the distal-most stratum 430 in the luer end 112 of syringe 100, which is angled further away from axis 514, and then further downward and outward through filter 274.

Upon contact with material 360, e.g., an absorbent powder, in distal-most portion 332, removed denser substances 435 may turn into a solid or gel-like substance 361 in distal-most portion 332 of insert cavity 310. The removed denser substances 435 may remain in the insert 300, as illustrated in FIG. 27, and may be disposed with the insert 300, after the removal from the insert 300 of syringes 100 with strata 410 and 420 of oil 415 and fat 425, and assemblies 200 coupled with the syringes. As described above, the off-center or offset position of opening 130 on the luer end 112 of syringe 100 allows for the elimination of more of the denser substances 415 including the tumescent fluid from syringe 100 when syringe 100 is in an angled vertical position during centrifugation, without trapping any residual substances or fluid in the chamber 120 of syringe 100, as illustrated in FIGS. 18 and 19.

The denser substances 435 in stratum 430 may also be removed from syringe 100 through filter 274 after centrifugation. In this case, the filter 274 is blocked with cover 275 during centrifugation, illustrated in FIGS. 5 and 6. Once syringe 100 is stationary, cover 275 is removed, and denser substances 435 are permitted to drain or be filtered out through filter 274.

Regardless of whether denser substances 435 are removed during or after centrifugation, filter 274 does not permit passage of fat 425 from syringe 100. In other words, once denser substances 435 are removed through filter 274, the first fat 425 contacting or touching filter 274 creates an airtight seal protecting the rest of fat 425 from air contamination.

Oil 415 is extracted or removed from the proximal stratum 410 in syringe 100 either during or after centrifugation, as illustrated in FIGS. 3 and 28. Oil 415 may be removed during centrifugation if the plunger 160 includes a filter 169 covering opening 168 in plunger head 162, as described above, and as illustrated in FIG. 3. A closure 167 may be provided to selectively close the opening 168 and block off filter 169 during movement of plunger 160 in proximal direction 700 to draw substances 400 into syringe 100, and during movement of plunger 160 in distal direction 702 to push substances 400 out of syringe 100. In this case, during centrifugation, as denser substances 435 are filtered out through filter 274 at the luer end 112 of syringe 100, oil 415 moves in proximal direction 700 through filter 169 and out of syringe 100.

However, operators may want to collect extracted or removed oil 415 and use it for other purposes. In such a case, the syringe or insert may either have a collector 380 or another mechanism, component, device or member for collecting such extracted or removed oil 415, or the oil is extracted or removed after centrifugation in a more contained environment.

If operators prefer to extract or remove oil 415 after centrifugation, than a filter 169 is not necessary on port or valve 161. For removing oil 415 after centrifugation, the operator may first detach, disengage, decouple or otherwise remove insert 300 (with syringes 100 and their respective assemblies 200 and substances 400 contained therein) from rotatable centrifuge member 520, place insert 300 on surface 800, before opening insert cover 370, in order to maintain cleanliness of centrifuge 500, as illustrated in FIG. 27. The operator opens insert cover 370 and may operate on syringe 100 while syringe 100 is retained in insert cavity 310, as illustrated in FIG. 27, or removes syringe 100 from insert cavity 310, before extracting or removing oil 415 therefrom. Once syringe 100 and plunger head 162 is exposed, operator may aspirate or draw or extract oil 415 out from the proximal-most stratum 410 through aspiration valve or port 161 and opening 168, as illustrated in FIG. 28.

The syringe 100 then contains only fat 425. The operator may then use the same valve or port 161 and opening 168 to inject additional substances into syringe 100, e.g., hormones or cleaning solutions which may be regarded as increasing the viability of the fat 425. These additional substances may be left mixed in with fat 425, or centrifuged out again, in a second centrifuging process.

Regardless of whether additional substances are introduced into syringe 100, the fat 425 is then transferred to a series of smaller syringes 600, e.g., 1 cc syringes, for injection, as illustrated in FIG. 29. The filter cap 274 illustrated in FIG. 5 or 6 is removed from assembly 200 by either breaking it off from adapter 230 or unscrewing it from adapter 230, leaving syringe 100 coupled with proximal end 232 of adapter 230. Syringe 600 is coupled with adapter 230, as illustrated in FIG. 7. Plunger shaft 164 is re-coupled or reattached with plunger head 162, and movement of plunger 160 in distal direction 702 pushes fat 425 (and any additional substances, if any) out from syringe 100, through passageway 236 in adapter 230, and into syringe 600, as illustrated in FIG. 29.

The fat 425 is thus collected and prepared for being injected into the desired location with syringe 600.

The system and process for collecting and preparing fat 425 may be modified to increase a percentage of more viable fat tissue 426 (e.g., viable unruptured fat cells) in the fat 425 that has been collected and prepared for transplantation. A higher percentage of viable fat tissue 426 in a prepared sample will provide greater long term results after transplantation. More viable fat tissue 426 has a higher density or specific gravity than less viable fat tissue 427. During and/or after centrifugation, more viable fat tissue 426 tends to settle into or be in a more distal or lower layer 428 of fat stratum 420, while less viable fat tissue 427 tends to settle into or be in a more proximal region or superficial layer 429 of fat stratum 420. Removal of some or all of the less viable fat tissue 427 from the fat 425 in syringe 100, increases a percentage of more viable fat tissue 426 in fat 425 prepared for transplant. However, it may be difficult to delineate or distinguish the superficial layer 429 from the lower layer 428 in fat stratum 420.

Figure 30:
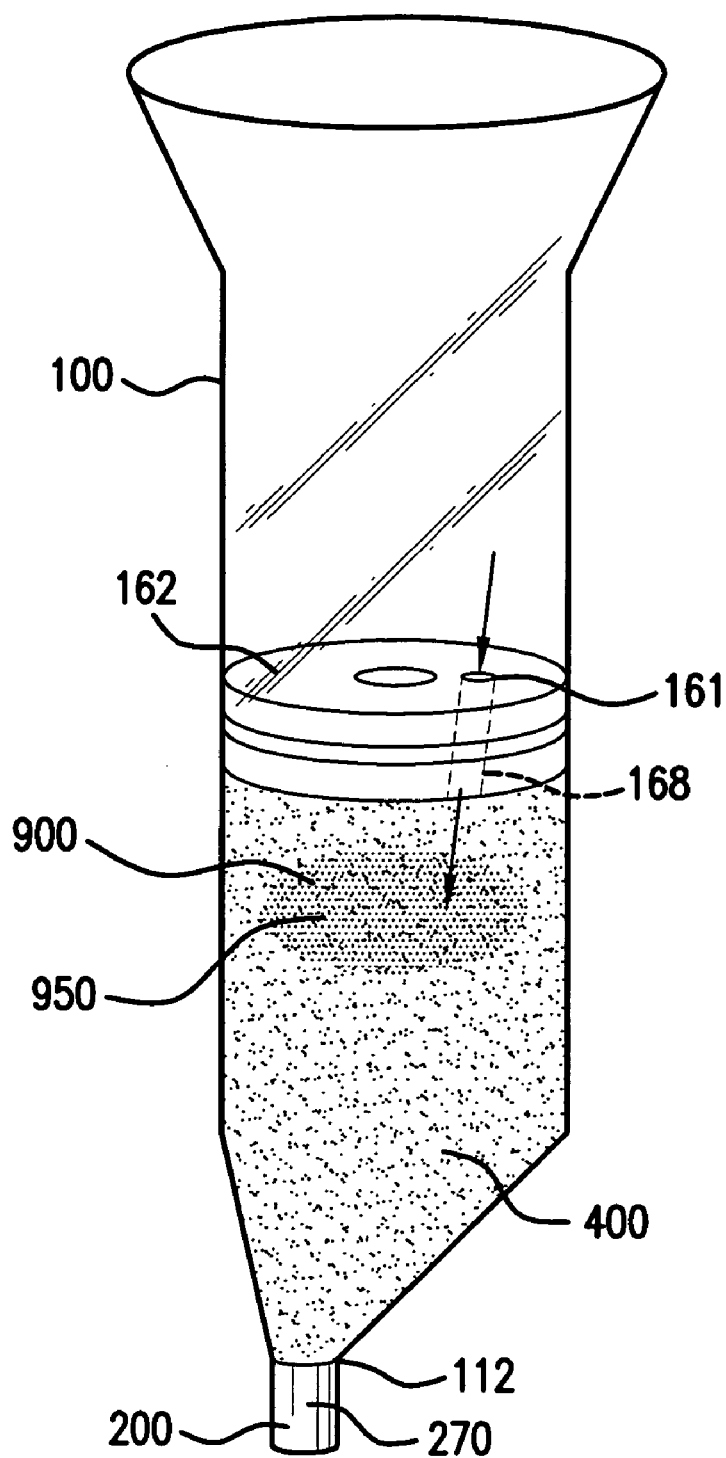
FIG. 30 illustrates a perspective view of an embodiment of a fat collection and preparation system according to the present invention.
Figure 31:
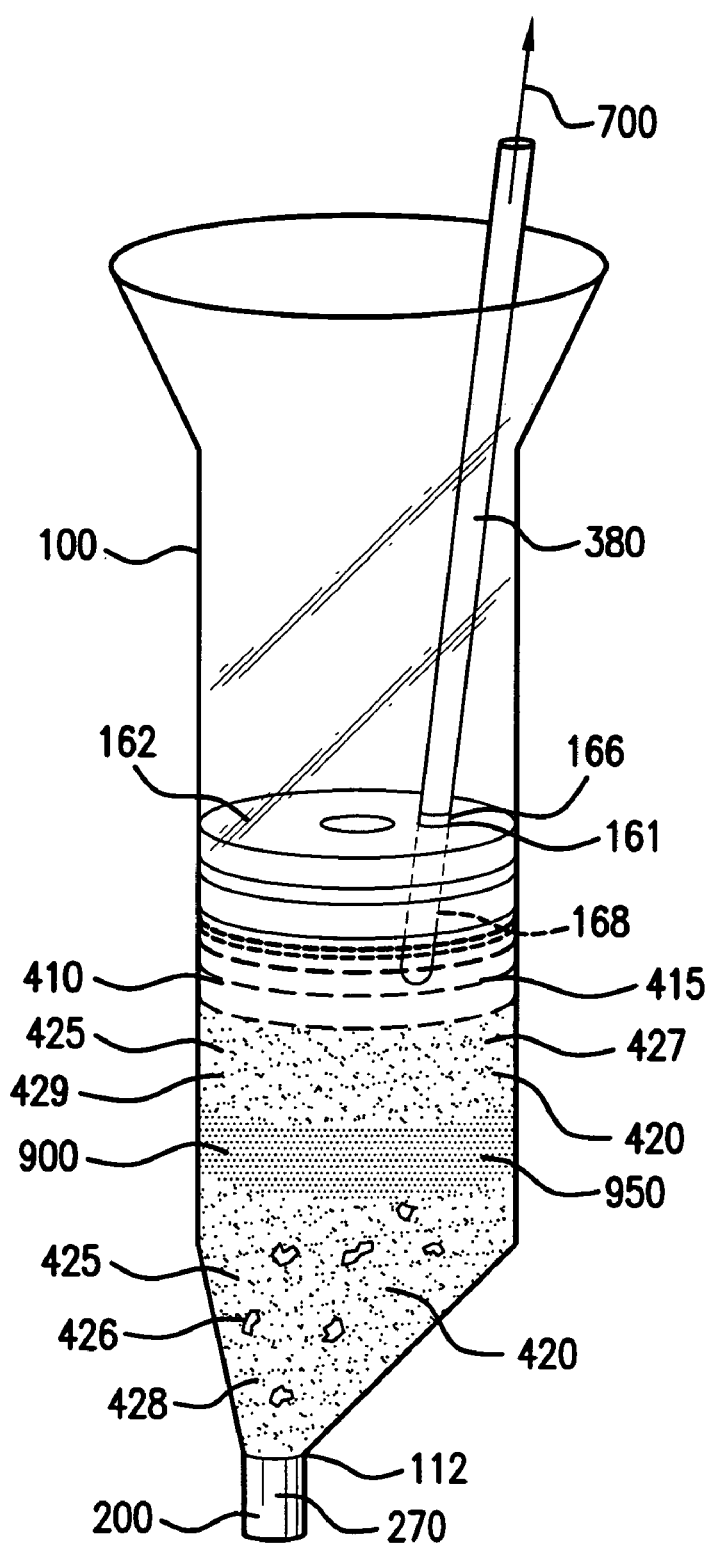
FIG. 31 illustrates a perspective view of an embodiment of a fat collection and preparation system according of FIG. 30.

In an embodiment, as illustrated in FIGS. 30 and 31, a marking substance 900 is introduced into the mixture 400 either into the fat harvesting by being injected along with tumescent fluids before harvesting, or into the syringe 100 before a centrifugation of the syringe. Marking substance 900 may be a solution including a substance, e.g, a non-toxic dye 950 (such as food coloring or an FDA-approved marking substance), which has a density or specific gravity equal to or higher than a density or specific gravity of the less viable fat tissue 427 (such as an average or maximum density or specific gravity of the less viable fat tissue). Alternatively, dye 950 may have a density or specific gravity equal to or less than a density or specific gravity of the more viable fat tissue 426 (such as an average or minimum density or specific gravity of the more viable fat tissue). Dye 950 may also have a density or specific gravity less than a density or specific gravity of the denser substances 435 in the distal most stratum.

After centrifugation, some or all of the superficial layer 429 has a different color than the lower layer 428, or a colored line or layer may appear delineating a boundary between the superficial layer 429 and the lower layer 428. In either case, a visual distinction is created that enables an operator to remove some or all of the superficial layer 429 during or after removing oil 415 from the mixture 400, while leaving a higher percentage of more viable fat tissue 426 in fat 425 in the syringe 100. Some or all of the superficial layer 429 can be extracted or otherwise removed through aspiration valve or port 161 and opening 168, or through another opening in plunger head 162, either while syringe 100 is resting or retained in insert cavity 315, or once syringe 100 has been removed from insert cavity 315.

Specifically, dye 950 may be introduced or injected in syringe 100 at any time before a first or subsequent centrifugation. Dye 950 may be provided (or pre-loaded or automatically included) in syringe 100 before harvesting, or dye 950 may be injected into syringe 100 through valve 161 or through another opening in plunger head 162 before or after inserting or placing the syringe 100 and its respective assembly 200 in centrifuge insert 300, or before or after coupling the syringe 100 with its respective assembly 200. Alternatively, an operator may inject dye 950 into syringe 100 prior to a second or a subsequent centrifugation, after the denser substances 435 and oil 415 have been removed from syringe 100 (e.g., either before, during or after the operator is injecting additional substances e.g., hormones or cleaning solutions into syringe 100 that are added to increase the viability of fat 425 as described above). In any case, the fat 425 that is eventually collected and prepared may contain a higher percentage of more viable fat tissue 426 for transplantation.

Additionally, the injection of a marking substance 900 and centrifuging the mixture 400 or the fat 425 with the marking substance 900, will provide an operator with feedback on the collection and preparation system and process. For example, an operator may adjust any aspect of the process or system in order to maximize a percentage of more viable fat tissue 426 in the collected and prepared fat 425, based on a measurement of the less viable fat tissue 427 that is removed from fat 425 or a measurement of the more viable fat tissue 426 that remains in the collected and prepared fat 425. The measurement may be obtained by measuring a quantity of removed less viable fat tissue 427 after its removal, or by visually ascertaining a location or position of the delineation between the superficial layer 429 and the lower layer 428 in fat stratum 420 after centrifugation.

The collection and preparation process and system may be adjusted between patients, or it may be adjusted for each specific patient. For example, an operator may collect and/or prepare a first sample of fat 425 from a patient, and after measuring a percentage of more viable fat tissue 426 or less viable fat tissue 427 in fat 425, the operator may adjust part or all of the system or process before collecting and preparing a subsequent fat sample from the same patient, e.g., by altering the speed or duration of centrifuging, or the dimensions of the cannula or the power of the aspirator used during the harvesting process.

In the preceding specification, the present invention has been described with reference to specific exemplary embodiments thereof. It will, however, be evident that various modifications and changes may be made thereunto without departing from the broader spirit and scope of the present invention as set forth in the claims that follow. The specification and drawings are accordingly to be regarded in an illustrative rather than restrictive sense.

What is claimed is:

1. A method of preparing fat for transplantation, comprising the steps of:

mating a distal end of a first syringe with a first end of an adapter assembly;

engaging a filter assembly with a second end of the adapter assembly, the filter assembly including a filter attached thereto;

after the engaging and mating steps, inserting the first syringe into a receiver in a centrifuge insert, a combination of substances releasably retained inside a chamber of the syringe, the combination of substances including oil, fat and a denser substance;

after the engaging and mating steps, coupling the centrifuge insert to a rotatable centrifuge member of a centrifuge;

after the coupling step, centrifuging the first syringe to stratify the combination of substances into strata of oil, fat and the denser substance;

before the centrifuging step, introducing a marking substance into the first syringe;

after the coupling step, filtering at least a portion of the denser fluid stratum from the first syringe through the filter, the filter preventing passage of at least a portion of the fat stratum from the first syringe;

after the coupling step, extracting at least a portion the oil stratum from an opening in a plunger head in a proximal portion of the syringe; and after the centrifuging step, removing at least a portion of a less viable fat tissue from the fat stratum in the first syringe.

2. The method according to claim 1, wherein the introducing step includes the step of:

after the coupling step, injecting a dye into the syringe, the dye being the marking substance, the dye having one of a density and a specific gravity that is one of equal to or higher than one of a density and a specific gravity of the less viable fat tissue.

3. The method according to claim 1, wherein the introducing step includes the substep of:

after the coupling step, injecting a dye into the syringe, the dye being the marking substance, the dye having one of a density and a specific gravity that is one of equal to or less than one of a density and a specific gravity of a more viable fat tissue in the fat stratum.

4. The method according to claim 1, wherein the removing step is performed after the extracting step.

5. The method according to claim 1, wherein the removing step is performed contemporaneously with the extracting step.

6. The method according to claim 1, wherein the introducing step is performed before the mating step.

7. A method comprising the steps of:

centrifuging a combination of substances and a dye in a chamber in a syringe, to separate the combination of substances in the chamber into strata according to a density of each of the substances in the combination, a plunger head slidably and sealingly inserted into an open proximal end of the chamber, a distal end of the chamber having an opening, a center of the opening offset from a central longitudinal axis of the chamber; and after the centrifuging step, removing one of: at least a portion of the substances above the dye from the chamber, and at least a portion of the substances together with at least a portion of the dye from the chamber.

8. The method according to claim 7, wherein the centrifuging step includes the substep of:

removing a distal stratum of densest substances from the chamber through a filter in an assembly releasably coupled with the opening, the filter preventing passage of less dense substances from the chamber.

9. The method according to claim 8, further comprising the step of:

after the centrifuging step, attaching the plunger shaft to the plunger head.

10. The method according to claim 9, further comprising the step of:

after the attaching step, transferring at least a portion of the less dense substances into a second syringe.

11. The method according to claim 10, wherein the transferring step includes the substep of:

depressing a proximal end of the plunger shaft to move the plunger head in a distal direction and to push the portion of the less dense substances out of the chamber through the opening and the assembly into the second syringe.

* * * * *